US009884019B2

(12) United States Patent
Tchessalov et al.

(10) Patent No.: US 9,884,019 B2
(45) Date of Patent: Feb. 6, 2018

(54) LYOPHILIZATION ABOVE COLLAPSE

(75) Inventors: Serguei Tchessalov, Andover, MA (US); Dan Dixon, Arlington, MA (US); Nicholas Warne, Andover, MA (US)

(73) Assignee: Wyeth LLC, New York, NY (US)

( * ) Notice: Subject to any disclaimer, the term of this patent is extended or adjusted under 35 U.S.C. 154(b) by 703 days.

(21) Appl. No.: 12/536,321

(22) Filed: Aug. 5, 2009

(65) Prior Publication Data
US 2010/0041870 A1 Feb. 18, 2010

Related U.S. Application Data

(60) Provisional application No. 61/086,426, filed on Aug. 5, 2008.

(51) Int. Cl.
| | |
|---|---|
| *A61K 9/19* | (2006.01) |
| *A61K 38/00* | (2006.01) |
| *A61K 38/22* | (2006.01) |
| *A61K 38/43* | (2006.01) |
| *A61K 39/00* | (2006.01) |
| *A61K 39/395* | (2006.01) |
| *A61K 47/02* | (2006.01) |
| *A61K 47/10* | (2017.01) |
| *A61K 47/26* | (2006.01) |
| *A61K 39/12* | (2006.01) |
| *A61K 47/18* | (2017.01) |

(52) U.S. Cl.
CPC ...................................... *A61K 9/19* (2013.01)

(58) Field of Classification Search
CPC ................................ A61K 9/19; A61K 9/2095
See application file for complete search history.

(56) References Cited

U.S. PATENT DOCUMENTS

| | | | | |
|---|---|---|---|---|
| 5,298,261 | A * | 3/1994 | Pebley | A61K 9/2095 424/464 |
| 2004/0076666 | A1 * | 4/2004 | Green | A61K 9/0056 424/465 |
| 2007/0172479 | A1 * | 7/2007 | Warne et al. | 424/145.1 |

FOREIGN PATENT DOCUMENTS

| | | | |
|---|---|---|---|
| WO | WO-1994/14422 A1 | 7/1994 | |
| WO | WO 9533446 A1 * | 12/1995 | ........... A61K 9/0007 |
| WO | WO-2005/117962 A1 | 12/2005 | |
| WO | WO-2006/29467 A1 | 3/2006 | |
| WO | WO-2006/81320 A2 | 8/2006 | |
| WO | WO 2006081320 A2 * | 8/2006 | |

OTHER PUBLICATIONS

Colandene et al., Journal of Pharmaceutical Sciences, vol. 96 (6) pp. 1598-1608 (Jun. 2007).*
Johnson et al., Journal of Pharmaceutical Sciences, vol. 91 (4) pp. 914-922 (Apr. 2002).*
Adams et al., Journal of Chemical Technology and Biotechnology, 58: 71-76 (1993).*
Lewis et al., AAPS PharmSciTech, 11:1580-1589 (2010).*
Modern Pharmaceutics, Banker, et al. Eds., CRC Press, (2002) p. 600-601.*
Johnson 2011, American Pharmaceutical Review, 14(3) accessed online at http://www.americanpharmaceuticalreview.com/Featured-Articles/37021-Freeze-Drying-Protein-Formulations-above-their-Collapse-Temperatures-Possible-Issues-and-Concerns on Apr. 19, 2015.*
Ma et al., Pharmaceutical Research, 18: 196-202 (2001).*
Chang et al., Pharmaceutical Research, 13: 234-349 (1996).*
Lui et al., Pharmaceutical Development and Technology, 11: 3-28 (2006).*
Rambhatla et al., Pharmaceutical Development and Technology, 10: 33-40 (2005).*
Sacha et al., Journal of Pharmaceutical Sciences, 98: 3397-3405 (2009).*
Knopp et al., Food Science and Pharmacology, 54: 659-672 (1998).*
Albett et al., J. Chem. Soc. Faraday Trans, 88: 789-794 (1992).*
Attachment 3, Department of Health and Human Services, downloaded from https://www.fda.gov/ohrms/dockets/ac/06/briefing/2006-4228B1-04-FDA-PotencyStabilityredacted.pdf on Jun. 12, 2017.*
International Search Report for PCT/US09/52852 (dated Jan. 2010).
Written Opinion for PCT/US09/52852 (dated Jan. 2010).
Adams et al. (1996) "Optimizing the lyophilization cycle and the consequences of collapse on the pharmaceutical acceptability of Erwinia L-Asparaginase," J. of Pharmaceutical Sciences, 8606(12).
Bellows et al. (1972) "Freeze-drying of aqueous solutions: maximum allowable operating temperature," Cryobiology, 9:559-561.
Carpenter et al. (1997) "Rational design of stable lyophilized protein formulations: some practical advice," Pharmaceutical Research 14(8):969-975.
Chatterjee et al. (2005) "Partially crystalline systems in lyophilization :II. Withstanding collapse at high primary drying temperatures and impact on protein recovery, Journal of Pharmaceutical Sciences," 94(4):809-820.
MacKenzie, A.P. (1974) "Collapse during freeze-drying-Qualitative and quantitative aspects. In Freeze-Drying and Advanced Food Technology," Goldblith, S.A., Rey.L, Rothmayr, W.W., Eds.; Academic Press, New York, pp. 277-307.
Nail et al. (2002) "Fundamentals of freeze-drying," In: Development and manufacture of protein pharmaceuticals. Nail S. L., ed. New York: Kluwer Academic/Plenum Publishers, pp. 281-235.
Passot et al. (2007) "Effect of product temperature during primary drying on the long-term stability of lyophilized proteins," Pharm. Dev. and Tech., 12:543-553.
Pikal et al. (1990) "The collapse temperature in freeze-drying: dependence of measurement methodology and rate of water removal from the glassy phase," International Journal of Pharmaceutics, 62:165-186.

(Continued)

*Primary Examiner* — Kortney L. Klinkel
*Assistant Examiner* — Lisbeth C Robinson

(57) ABSTRACT

The present invention provides methods of lyophilizing a pharmaceutical substance involving a primary drying step executed at a product temperature at or above the collapse temperature. The invention also provides pharmaceutical substances lyophilized at or above the collapse temperature.

38 Claims, 20 Drawing Sheets

(56) References Cited

OTHER PUBLICATIONS

Pikal, M. J. (1990) "Freeze-drying of proteins. Part 1: process design," BioPharm., 3:18-26.
Pikal, M.J. (1990) "Freeze-drying of proteins. Part 2: formulation selection," BioPharm. 3:26-30.
Shalaev et al. (2002) "Thermophysical properties of pharmaceutically compatible buffers at sub-zero temperatures: implications for freeze-drying", Pharmaceutical Research, 19(2):195-201.
Tang et al. (2004) "Design of freeze-drying processes for pharmaceuticals: Practical advice," Pharm. Res., 21:191-200.
Wang et al. (2000) "Lyophilization and development of solid protein pharmaceuticals," Int. J. Pharm., 203:1-60.
Wang et al. (2004) "Nail Effect of collapse on the stability of freeze-dried recombinant factor VIII and a-Amylase," Journal of Pharmaceutical Sciences, 93(5):1253-1263.
Williams et al. (1984) "The lyophilization of pharmaceuticals; A literature review." J. Parenteral Sci. Technol., 38:48-59.
Depaz et al., "Freeze-Drying Above the Glass Transition Temperature in Amorphous Protein Formulations While Maintaining Product Quality and Improving Process Efficiency", J. of Pharmaceutical Sciences, vol. 105, pp. 40-49, 2016.
Dixon et al., "The Impact of Protein Concentration and Mannitol and Sodium Chloride Crystallinity and Polymorphism upon Lyophilization", J. of Pharmaceutical Sciences, vol. 98, No. 9, pp. 3419-3429 , 2009.
Pipe et al., "Functional factor VIII made with von Willebrand factor at high levels in transgenic milk" J. Thromb. Haemost., vol. 9, No. 11, pp. 2235-2242, Nov. 2011.
Kathrin Brigitte Schersch, "Effect of Collapse on Pharmaceutical Protein Lyophilizates" Cuvillier Verlag Gottingen, Chapter 1, Publication Date: Feb. 3, 2011, downloaded from https://cuvillier.de/de/shop/publications/471, 10 pages.
Schersch et al., "Systematic Investigation of the Effect of Lyophilizate Collapse on Pharmaceutically Relevant Proteins I: Stability after Freeze-Drying", J. of Pharmaceutical Sciences, vol. 99, No. 5, pp. 2256-2278, 2010.

\* cited by examiner

LYOPHILIZATION ABOVE COLLAPSE

RELATED APPLICATIONS

This application claims priority to U.S. Provisional Patent Application Ser. No. 61/086,426, filed on Aug. 5, 2008; the entirety of which is hereby incorporated by reference.

BACKGROUND OF THE INVENTION

Lyophilization, or freeze-drying, is a process widely used in the pharmaceutical industry for the preservation of biological and pharmaceutical materials. In lyophilization, water present in a material is converted to ice during a freezing step and then removed from the material by direct sublimation under low-pressure conditions during a primary drying step. During freezing, however, not all of the water is transformed to ice. Some portion of the water is trapped in a matrix of solids containing, for example, formulation components and/or the active ingredient. The excess bound water within the matrix can be reduced to a desired level of residual moisture during a secondary drying step. All lyophilization steps, freezing, primary drying and secondary drying, are determinative of the final product properties.

However, primary drying is typically the longest step in a lyophilization process. Therefore, optimization of this portion of the process has significant economic effect (Pikal et al. "Freeze-drying of proteins. Part 2: formulation selection," *BioPharm* 3:26-30 (1990); Pikal et al. "The collapse temperature in freeze-drying: dependence of measurement methodology and rate of water removal from the glassy phase," *International Journal of Pharmaceutics*, 62 (1990), 165-186). For many years, cycle and formulation optimization was performed to assure that the product temperature during primary drying would never exceed the collapse temperature. The collapse temperature is the product temperature during freeze-drying above which product cake begins to lose its original structure. It was reported in literature that, above the collapse temperature, product could experience slow sporadic bubbling, swelling, foaming, cavitation, fenestration, gross collapse, retraction and beading that may have consequences on the appearance of the product (MacKenzie, "Collapse during freeze-drying-Qualitative and quantitative aspects" In *Freeze-Drying and Advanced Food Technology*; Goldblith, S. A., Rey. L, Rothmayr, W. W., Eds.; Academic Press, New York, 1974, 277-307). As a result, it is thought that collapse results in poor product stability, long drying times (due to pore's collapse), uneven drying and loss of texture (R. Bellows, et al. "Freeze-drying of aqueous solutions: maximum allowable operating temperature," *Cryobiology*, 9, 559-561 (1972). For proteins, collapse during freeze-drying has been reported to lead to elevated moisture, increased degradation rate and reconstitution time (Carpenter, J. F. et al. "Rational design of stable lyophilized protein formulations: some practical advice," *Pharmaceutical Research* (1997), 14(8): 969-975; Adams et al. "Optimizing the lyophilization cycle and the consequences of collapse on the pharmaceutical acceptability of *Erwinia* L-Asparaginase," *J. of Pharmaceutical Sciences*, Vol. 8606, No. 12, December (1996); S. Passot et al. "Effect of product temperature during primary drying on the long-term stability of lyophilized proteins," *Pharm. Dev. and Tech.*, 12:543-553, 2007). Therefore, for many years, it was considered critical to freeze-dry under the collapse temperature.

SUMMARY OF THE INVENTION

The present invention encompasses the discovery that freeze-drying may be carried out above the collapse temperature while still retaining product stability, biological activity and other important product attributes. Thus, the present invention provides, among other things, improved lyophilization methods with significantly shortened primary drying step.

In one aspect, the present invention provides methods of lyophilizing a liquid formulation including a primary drying step executed at a product temperature at or above the collapse temperature. In some embodiments, inventive methods include a primary drying step executed without avoiding collapse (e.g., micro-collapse, visually detectable, or macro-collapse) in the lyophilized products. In some embodiments, the liquid formulation contains a pharmaceutical substance (e.g., protein) at a concentration of at least about 1 mg/ml (e.g., at least about 10 mg/ml, at least about 50 mg/ml, at least about 100 mg/ml, at least about 150 mg/ml, at least about 200 mg/ml, at least about 250 mg/ml, at least about 300 mg/ml, or at least about 400 mg/ml).

In some embodiments, the liquid formulation is a sucrose-based formulation.

In some embodiments, the liquid formulation is formulated such that the collapse temperature is at least 1° C. higher than the middle point of glass transition temperature (Tg'). In some embodiments, the liquid formulation is formulated such that the collapse temperature is at least 2° C. higher than the middle point of glass transition temperature (Tg'). In some embodiments, the liquid formulation is formulated such that the collapse temperature is at least 5° C. higher than the middle point of glass transition temperature (Tg'). In some embodiments, the liquid formulation is formulated such that the collapse temperature is at least 10° C. higher than the middle point of glass transition temperature (Tg').

In some embodiments, the primary drying is executed at the collapse temperature or a temperature above collapse but below the eutectic melting temperature (e.g., at least 10° C., 2° C., 3° C., 4° C., 5° C., 6° C., 7° C., 8° C., 9° C., 10° C. above collapse).

In another aspect, the present invention provides methods of lyophilizing a liquid formulation including a primary drying step at a product temperature at or above the collapse temperature, wherein the liquid formulation includes a pharmaceutical substance (e.g., protein) and a stabilizing agent. In some embodiments, the ratio of the mass amount of the stabilizing agent and the pharmaceutical substance is no greater than 1000 (e.g., no greater than 500, no greater than 100, no greater than 50, no greater than 10, no greater than 1, no greater than 0.5, no greater than 0.1).

In some embodiments, the pharmaceutical substance is at a concentration of at least about 1 mg/ml (e.g., at least about 10 mg/ml, at least about 50 mg/ml, at least about 100 mg/ml, at least about 150 mg/ml, at least about 200 mg/ml, at least about 250 mg/ml, at least about 300 mg/ml, or at least about 400 mg/ml).

In some embodiments, the stabilizing agent is selected from the group consisting of sucrose, mannose, sorbitol, raffinose, trehalose, glycine, mannitol, sodium chloride, arginine, lactose, hydroxyethyl starch, dextran and polyvinylpyrrolidone and combinations thereof.

In a further aspect, the present invention provides methods of storing a pharmaceutical substance (e.g., protein) including steps of: (a) lyophilizing the pharmaceutical substance in a liquid formulation comprising a primary drying step executed at a product temperature at or above the collapse temperature; (b) storing the lyophilized pharmaceutical substance for a period longer than 3 months (e.g., longer than 8 months, longer than 12 months, longer than 18 months, longer than 24 months).

In some embodiments, the pharmaceutical substance is at a concentration of at least about 1 mg/ml (e.g., at least about 10 mg/ml, at least about 50 mg/ml, at least about 100 mg/ml, at least about 150 mg/ml, at least about 200 mg/ml, at least about 250 mg/ml, at least about 300 mg/ml, or at least about 400 mg/ml).

In some embodiments, the liquid formulation further contains a stabilizing agent. In some embodiments, the stabilizing agent is selected from the group consisting of sucrose, mannose, sorbitol, raffinose, trehalose, glycine, mannitol, sodium chloride, arginine, lactose, hydroxyethyl starch, dextran and polyvinylpyrolidone and combinations thereof.

In some embodiments, the lyophilized product in accordance with the present invention may contain amorphous materials (e.g., fully amorphous materials). In some embodiments, the lyophilized product in accordance with the present invention may contain partly crystalline/partly amorphous materials.

In some embodiments, the present invention provides methods of improving the stability of a lyophilized pharmaceutical substance (e.g., protein) or the efficiency of the lyophilization cycle by lyophilizing the pharmaceutical substance (e.g., protein) in a liquid formulation at a product temperature at or above the collapse temperature.

In some embodiments, the present invention provides methods of evaluating a batch of lyophilized product including steps of (a) evaluating one or more samples from the batch of the lyophilized product, wherein at least one sample is characterized with cake collapse (e.g., micro-collapse, visually-detectable or macro-collapse); and (b) releasing the batch of the lyophilized product based on the evaluation result from step (a).

In some embodiments, step (a) includes a step of measuring the residual moisture of the one or more samples. In some embodiments, step (a) includes a step of determining the stability profile of the one or more samples. In some embodiments, the step of determining the stability profile includes determining a degradation rate. In some embodiments, the degradation rate is determined by a method selected from the group consisting of SE-HPLC, RP-HPLC, CEX-HPLC, MALS, fluorescence, ultraviolet absorption, nephelometry, CE, and combinations thereof. In some embodiments, step (a) includes a step of determining an activity of the lyophilized product. In some embodiments, the activity can be determined by various activity assays (e.g., cell based, ELISA, enzymatic assays).

In some embodiments, the lyophilized product contains a polysaccharide and step (a) includes a step of measuring the conjugation efficiency of the polysaccharide to a carrier protein.

In some embodiments, step (a) includes a step of determining the reconstitution time.

In some embodiments, step (a) does not include a step of evaluating the cake appearance of the one or more samples.

In some embodiments, the present invention provides methods of preparing a pharmaceutical substance (e.g., protein) including steps of: (a) providing a lyophilized pharmaceutical substance (e.g., protein) characterized with cake collapse (e.g., micro-collapse, visually-detectable or macro-collpase); (b) reconstituting the lyophilized pharmaceutical substance, wherein the reconstituted pharmaceutical substance is biologically or pharmaceutically active.

Inventive methods in accordance with the present invention can be utilized to lyophilize, store, evaluate, and/or prepare pharmaceutical substances, including but not limited to, proteins, nucleic acids (e.g., RNAs, DNAs, or RNA/DNA hybrids, aptamers), chemical compounds, polysaccharides, small molecules, drug substances, natural products, immunogens, vaccines, carbohydrates, and combinations thereof. As used herein, the term "protein" refers to a polypeptide (i.e., a string of at least two amino acids linked to one another by peptide bonds) or combinations of polypeptides. Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), synthetic polypeptides, or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, glycosylation, etc. In some embodiments, proteins may comprise natural amino acids, non-natural amino acids, synthetic amino acids, and combinations thereof. Exemplary proteins include, but are not limited to, antibodies (e.g., monoclonal antibodies) or fragments thereof, growth factors, clotting factors, cytokines, fusion proteins, polysaccharide-containing antigens, pharmaceutical drug substances, vaccines (e.g., killed-virus vaccines, attenuated-virus vaccines, toxoid vaccines, subunit vaccines, multi-valent vaccines, conjugate vaccines, live-virus vaccines, and individual components thereof, etc.), enzymes, Small Modular ImmunoPharmaceuticals (SMIP™). As used herein, antibodies or antibody fragments include, but are not limited to, intact IgG, F(ab')2, F(ab)2, Fab', Fab, ScFv, single domain antibodies (e.g., shark single domain antibodies (e.g., IgNAR or fragments thereof)), diabodies, triabodies, tetrabodies.

The present invention further provides proteins, nucleic acids (e.g., RNAs, DNAs, or RNA/DNA hybrids, aptamers), chemical compounds, small molecules, drug substances, natural products, polysaccharides, small molecules, drug substances, natural products immunogens, vaccines, carbohydrates, and/or other products lyophilized, stored, and/or prepared using inventive methods in accordance with the present invention.

As used in this application, the terms "about" and "approximately" are used as equivalents. Any numerals used in this application with or without about/approximately are meant to cover any normal fluctuations appreciated by one of ordinary skill in the relevant art. For example, normal fluctuations of a value of interest may include a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

DETAILED DESCRIPTION OF THE INVENTION

Figure 1:
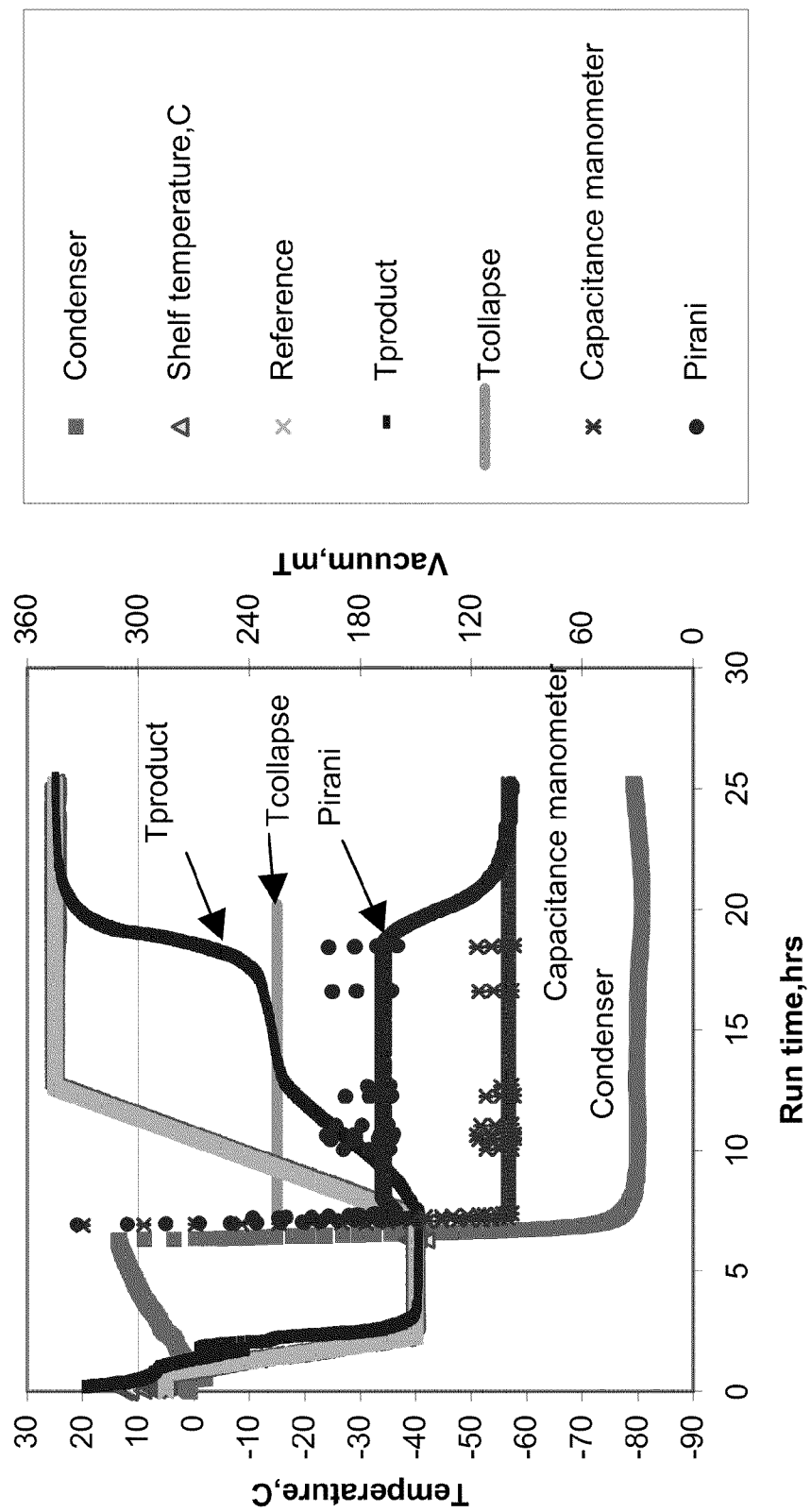
FIG. 1 illustrates an exemplary freeze-drying cycle graph of 50 mg/ml molecule G at temperature above the collapse temperature: aggressive cycle. The formulation also contains 5% sucrose, 10 mM Histidine, 10 mM methionine and 0.01% polysorbate-80.

The present invention provides highly efficient and cost-effective lyophilization methods. Among other things, the present invention provides methods of lyophilizing liquid formulations including a primary drying step at a product temperature at or above the collapse temperature. Inventive methods in accordance with the present invention are particularly useful for freeze-drying liquid formulations containing high concentrations of proteins or other pharmaceutical substances. In some embodiments, inventive methods in accordance with the present invention improve the stability of lyophilized products.

Lyophilization, also known as freeze-drying, is often used to store pharmaceutical drug products because chemical and physical degradation rates of the drug products may be significantly reduced in the dried state, allowing for longer product shelf life. However, lyophilization typically adds significantly to the cost of drug manufacturing. This cost can be minimized by developing a cycle that consumes the least amount of time without jeopardizing product quality or stability. For example, increasing product temperature by 1° C. degree during lyophilization could result in 13% decrease of primary drying time. See, Pikal et al. "The collapse temperature in freeze-drying: dependence of measurement methodology and rate of water removal from the glassy phase," *International Journal of Pharmaceutics*, 62 (1990), 165-186.

Lyophilization includes several steps such as freezing, primary drying, and secondary drying. See, Tang X., et al. (2004) "Design of freeze-drying processes for pharmaceuticals: Practical advice," *Pharm. Res.*, 21:191-200; Nail S. L., et al. "Fundamentals of freeze-drying," In: Development and manufacture of protein pharmaceuticals. Nail S. L., ed. New York: Kluwer Academic/Plenum Publishers, pp 281-353; Wang, et al. "Lyophilization and development of solid protein pharmaceuticals," *Int. J. Pharm.*, 203:1-60; Williams N. A., et al. "The lyophilization of pharmaceuticals; A literature review." *J. Parenteral Sci. Technol.*, 38:48-59. The primary drying step, which involves sublimation of frozen or unbound water, is the most time-consuming step of the lyophilization cycle. Traditionally, it was considered critical to maintain the product temperature below its collapse temperature during the primary drying in order to keep intact microscopic structure of solid materials present in the frozen solution. It was thought that it is this structure that makes up the freeze-dried cake with a relatively high surface area, allowing low residual moisture and rapid reconstitution after freeze-drying.

As discussed in the Examples section, the present inventors have discovered that lyophilization, in particular, primary drying, may be executed at a product temperature above the collapse temperature while maintaining protein stability and other desirable quality attributes (e.g., residual moisture, reconstitution time, etc.). Even samples with apparent collapse (e.g., visually detectable collapse in vials), which would be normally rejected, exhibited a similar stability profile to the samples lyophilized below the collapse temperature. Moreover, in some cases, the stability of lyophilized products was improved by freeze-drying above the collapse temperature. For example, as a non-limiting example described in Example 2, partly crystalline/partly amorphous materials lyophilized well above the collapse temperature but slightly below the melting point of mannitol showed better stability than samples lyophilized below the collapse temperature. Thus, compared to the traditional lyophilization cycles, the present invention provides significant economic advantages by providing aggressive and/or fast lyophilization cycles with shorter primary drying time without jeopardizing protein quality and stability. In some cases, the present invention provides improved product stability.

Another advantage of this invention is an application to the assessment of deviations during the commercial manufacturing. If deviation of process parameters during existing commercial cycle (normally performed below the collapse temperature) results in visually detectable product collapse, the present inventors contemplate that the stability profile of the collapsed product may be comparable to the normal cycle if the residual moisture is within specification. Therefore, this particular batch containing samples with visually detectable cake collapse could be released. Thus, manufacturing of commercial batches with zero or substantially reduced reject rates is possible if the particular product could withstand the collapse. A development robustness study can be performed prior to commercial manufacturing to confirm if the stability of the collapsed materials is comparable to that of the control materials for each particular product.

As used herein, the term "collapse temperature (Tc)" refers to a temperature (e.g., product temperature) during freeze-drying at or above which the collapse occurs. As used herein, the term "collapse" refers to loss of an intact structure or change of the original structure of lyophilized cake. In some embodiments, collapse includes loss of a microscopic structure (also referred to as micro-collapse). In some embodiments, micro-collapse is visually undetectable. In some embodiments, micro-collapse refers to loss of less than about 1% (e.g., less than about 0.9%, 0.8%, 0.7%, 0.6%, 0.5%, 0.4%, 0.3%, 0.2%, 0.1%, 0.05%, or 0.01%) of the original intact structure (e.g., a lyophilized cake structure). In some embodiments, the temperature at or above which the micro-collapse occurs is referred to as the micro-collapse temperature. In some embodiments, collapse includes loss of gross structures (also referred to as gross collapse or macro-collapse). In some embodiments, the temperature at or above which the gross collapse occurs is referred to as the gross collapse temperature (or macro-collapse temperature). Typically, gross collapse or macro-collapse results in visually detectable collapse in the lyophilized product. As used herein, the terms "gross collapse," "macro-collapse," and "visually detectable collapse" are used inter-changeably. In some embodiments, gross collapse, macro-collapse or visually detectable collapse refers to loss of at least 0.1% (e.g., at least about 1%, 5%, 10%, 15%, 20%, 25%, 30%, 35%, 40%, 45%, 50%, 55%, 60%, 65%, 70%, 75%, 80%, 85%, 90%, 95%, or 100%) of the original intact structure (e.g., a lyophilized cake structure).

In some embodiments, the temperature at which collapse occurs may not be discrete. Instead, collapse may be a gradual process that takes place over a temperature range with the intact cake structure progressively disappearing over the temperature range. Typically, the initial change or loss of the intact structure during the lyophilization process is considered the onset of the collapse. The temperature at which this initial change was observed is typically referred to as the onset collapse temperature. The temperature at which the loss of the structure or the structure change appeared to be complete throughout the cake is referred to as the collapse complete temperature.

Collapse in the product during lyophilization may be detected by various instruments including, but not limited to, product temperature measurement devices, freeze-drying microscopy or instruments detecting electrical resistance. Collapse in lyophilized product (e.g., cake) may be detected manually by visual inspection, residual moisture, Differential Scanning Calorimetry (DSC), BET surface area.

Collapse phenomenon is sensitive to the nature of the materials involved. For example, sucrose dominated formulations are very sensitive to collapse especially if they also contain small molecular species such as salts and buffers (Shalaev et al. "Thermophysical properties of pharmaceutically compatible buffers at sub-zero temperatures: implications for freeze-drying," *Pharmaceutical Research* (2002), 19(2):195-201). In these formulations, collapse usually occurs at temperature close to the mid-point of glass transition. The viscosity of amorphous sucrose-salt-buffer systems is very low resulting in massive collapse of structure when product temperature exceeds this critical temperature during primary drying. Thus, traditionally, lyophilization is carried out under Tg' whenever possible.

When product concentration increases, it changes the structural resistance of cake to the collapse.

The present invention may be utilized to lyophilize liquid formulations containing various product concentrations. In some embodiments, the present invention is particularly useful to lyophilize liquid formulations containing pharmaceutical substance at high concentrations. For example, liquid formulations suitable for the present invention may contain a product (e.g., protein) of interest at a concentration of at least about 1 mg/ml, at least about 10 mg/ml, at least about 20 mg/ml, at least about 30 mg/ml, at least about 40 mg/ml, at least about 50 mg/ml, at least about 75 mg/ml, at least about 100 mg/ml, at least about 150 mg/ml, at least about 200 mg/ml, at least about 250 mg/ml, at least about 300 mg/ml, at least about 400 mg/ml. In some embodiments, liquid formulations suitable for the present invention may contain a product (e.g., protein) of interest at a concentration in the range of about 1 mg/ml to 400 mg/ml (e.g., about 1 mg/ml to 50 mg/ml, 1 mg/ml to 60 mg/ml, 1 mg/ml to 70 mg/ml, 1 mg/ml to 80 mg/ml, 1 mg/ml to 90 mg/ml, 1 mg/ml to 100 mg/ml, 100 mg/ml to 150 mg/ml, 100 mg/ml to 200 mg/ml, 100 mg/ml to 250 mg/ml, or 100 mg/ml to 300 mg/ml, or 100 mg/ml to 400 mg/ml).

In some embodiments, a suitable formulation contains one or more stabilizing agents (e.g., sucrose, mannose, sorbitol, raffinose, trehalose, glycine, mannitol, sodium chloride, arginine, lactose, hydroxyethyl starch, dextran or polyvinylpyrolidone). In some embodiments, the ratio of the mass amount of the stabilizing agent and the pharmaceutical substance (e.g., protein) is no greater than 1000 (e.g., no greater than 500, no greater than 250, no greater than 100, no greater than 50, no greater than 10, no greater than 1, no greater than 0.5, no greater than 0.1). In some embodiments, suitable liquid formulations further include one or more bulking agents such as sodium chloride, lactose, mannitol, glycine, sucrose, trehalose and hydroxyethyl starch. In some embodiments, suitable liquid formulations contain buffering agents such as tris, histidine, citrate, acetate, phosphate and succinate.

In some embodiments, liquid formulations suitable for the present invention contain amorphous materials. In some embodiments, liquid formulations suitable for the present invention contain a substantial amount of amorphous materials (e.g., sucrose-based formulations). In some embodiments, liquid formulations suitable for the present invention contain partly crystalline/partly amorphous materials.

Contrary to the traditional methods, the present invention allows freeze-drying temperatures well above Tg'. For example, in formulations with protein concentrations above 50 mg/ml, we observed that collapse during lyophilization measured by freeze-drying microscopy is about 5-7° C. higher than the mid-point of glass transition temperature (Tg'). Thus, the present invention allows freeze-drying at temperatures at least 1° C., 2° C., 3° C., 4° C., 5° C., 6° C., 7° C., 8° C., 9° C., or 10° C. above the mid-point of Tg'.

Lyophilized product in accordance with the present invention can be assessed based on product quality analysis, reconstitution time, quality of reconstitution, high molecular weight, moisture, glass transition temperature, and biological or biochemical activity. Typically, product quality analysis includes product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering detector (MALS), fluorescence, ultraviolet absorption, nephelometry, capillary electrophoresis (CE), SDS-PAGE, and combinations thereof. In some embodiments, evaluation of lyophilized product in accordance with the present invention does not include a step of evaluating cake appearance. Additionally, lyophilized product may be assessed based on biological or biochemical activities of the product, typically, after reconstitution.

Inventive methods in accordance with the present invention can be utilized to lyophilize any materials, in particular, pharmaceutical substances. As used herein, the term "pharmaceutical substances" refers to any compounds or entities that alter, inhibit, activate, or otherwise affect biological or chemical events in vivo or in vitro. For example, pharmaceutical substances may include, but are not limited to, proteins, peptides, nucleic acids (e.g., RNAs, DNAs, or RNA/DNA hybrids, aptamers), chemical compounds, polysaccharides, small molecules, drug substances, natural products, immunogens, vaccines, carbohydrates, and/or other products. In some embodiments, the present invention is utilized to lyophilize proteins including, but not limited to, antibodies (e.g., monoclonal antibodies) or fragments thereof, growth factors, clotting factors, cytokines, fusion proteins, polysaccharide antigens, pharmaceutical drug substances, vaccines, enzymes, Small Modular ImmunoPharmaceuticals™ (SMIP™). In some embodiments, the present invention is utilized to lyophilize antibodies or antibody fragments including, but not limited to, intact IgG, F(ab')2, F(ab)$_2$, Fab', Fab, ScFv, single domain antibodies (e.g., shark single domain antibodies (e.g., IgNAR or fragments thereof)), diabodies, triabodies, tetrabodies.

In some embodiments, the present invention is used to lyophilize vaccines or vaccine components. Suitable vaccines include, but are not limited to, killed-virus vaccines, attenuated-virus vaccines, toxoid vaccines, subunit vaccines, multi-valent vaccines, conjugate vaccines, live-virus vaccines. Suitable vaccine components include, but are not limited to, polysaccharides and carrier proteins. "Polysaccharides," as used herein, include, without limitation, saccharides comprising a plurality of repeating units, including, but not limited to polysaccharides having 50 or more repeat units, and oligosaccharides having 50 or less repeating units. Typically, polysaccharides have from about 50, 55, 60, 65, 70, 75, 80, 85, 90, or 95 repeating units to about 2,000 or more repeating units, and preferably from about 100, 150, 200, 250, 300, 350, 400, 500, 600, 700, 800, 900 or 1000 repeating units to about, 100, 1200, 1300, 1400, 1500, 1600, 1700, 1800, or 1900 repeating units. Oligosaccharides typically have about from about 6, 7, 8, 9, or 10 repeating units to about 15, 20, 25, 30, or 35 to about 40 or 45 repeating units. Suitable carrier proteins typically include bacterial toxins that are immunologically effective carriers that have been rendered safe by chemical or genetic means for administration to a subject. Examples include inactivated bacterial toxins such as diphtheria toxoid, $CRM_{197}$, tetanus toxoid, pertussis toxoid, E. coli LT, E. coli ST, and exotoxin A from Pseudomonas aeruginosa. Bacterial outer membrane proteins such as, outer membrane complex c (OMPC), porins, transferrin binding proteins, pneumolysis, pneumococcal surface protein A (PspA), pneumococcal adhesion protein (PsaA), or pneumococcal surface proteins BVH-3 and BVH-11 can also be used. Other carrier proteins, such as protective antigen (PA) of Bacillus anthracis and detoxified edema factor (EF) and lethal factor (LF) of Bacillus anthracis, ovalbumin, keyhole limpet hemocyanin (KLH), human serum albumin, bovine serum albumin (BSA) and purified protein derivative of tuberculin (PPD) can also be used.

The quality of lyophilized vaccine components can be assessed and determined by their ability to form a conjugate vaccine. For example, the quality of lyophilized polysaccharides can be determined by their ability to couple or conjugate to a carrier protein. Similarly, the quality of lyophilized carrier proteins can be determined by their ability to couple or conjugate to a polysaccharide. Various methods are known in the art to conjugate a polysaccharide to a carrier protein and the conjugation efficiency can be determined by various analytical methods including, but not limited to, percentage free protein, percentage free polysaccharide, molecular size distribution, saccharide-to-protein ratio ("SPR") and yield rate. Exemplary methods for determining conjugation efficiency are described in the Examples.

Additional pharmaceutical substances may include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, and imaging agents.

A more complete listing of pharmaceutical substances and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals," Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

Lyophilization may be performed in a container, such as a tube, a bag, a bottle, a tray, a vial (e.g., a glass vial), syringe or any other suitable containers. The containers may be disposable. Controlled freeze and/or thaw may also be performed in a large scale or small scale.

Inventive methods in accordance with the present invention can be carried out using various lyophilizers, such as, commercial-scale lyophilizers, pilot-scale lyophilizers, or laboratory-scale lyophilizers.

It should be understood that the above-described embodiments and the following examples are given by way of illustration, not limitation. Lyophilization methods in accordance with the present invention can be applied to any molecules (e.g., proteins) in general. For example, the molecules A-J used in the following examples can be any proteins, antibodies, nucleic acids, chemical compounds, vaccines, enzymes, polysaccharides, natural products, small molecules, or any other types of molecules. Various changes and modifications within the scope of the present invention will become apparent to those skilled in the art from the present description.

EXAMPLES

Example 1: Freeze-Drying at or Above Collapse Temperature for Completely Amorphous Materials In this example, molecule G was freeze-dried at the collapse temperature during primary drying step. The formulation contained 50 mg/ml molecule G, 5% sucrose, 10 mM Histidine, 10 mM methionine and 0.01% polysorbate 80 (13). An exemplary freeze-drying cycle at collapse temperature is shown in FIG. 1.

Figure 2:
FIG. 2 illustrates an exemplary cake appearance of molecule G after freeze-drying. Left vial represents drying above collapse temperature (FIG. 1), whereas the right vial was freeze-dried well below the Tg'.

As illustrated in FIG. 1, the product temperature ($T_{product}$, FIG. 1) did, in fact, exceed the collapse temperature ($T_{collapse}$, FIG. 1). Thorough visual analysis of cake appearance showed that the bottom of the cake did undergo some degree of collapse (left vial, FIG. 2).

Figure 3:
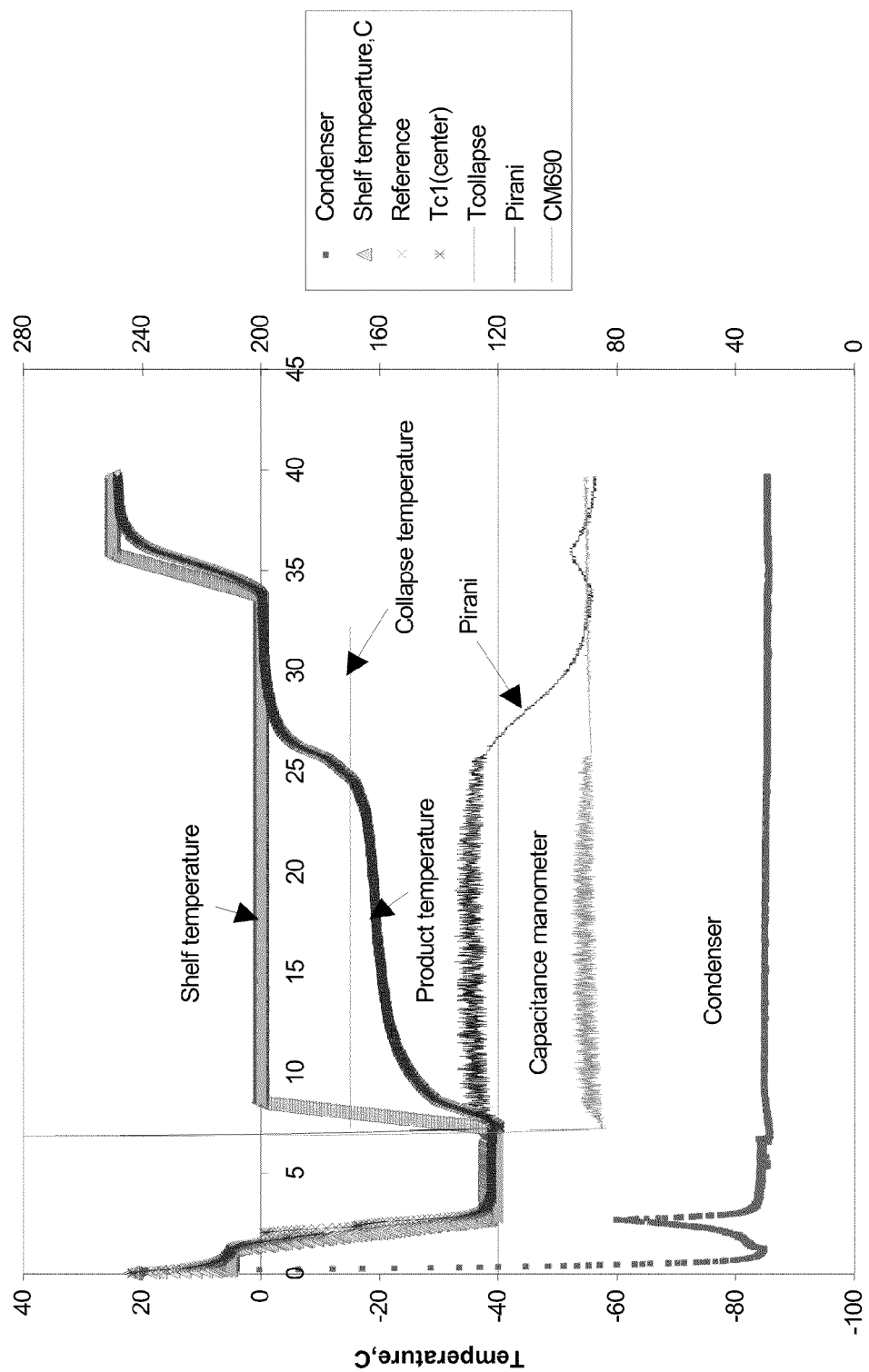
FIG. 3 illustrates an exemplary control cycle of molecule G.

However, despite the obvious collapse, the residual moisture of material from the collapsed cake (left vial) was similar to that of the normal or control cake (0.36% in collapsed cake versus 0.37% in the control material). Reconstitution time was also similar. It is important to notice that the lyophilization cycle above the collapse temperature (FIG. 1) was shorter than the control cycle (FIG. 3). The product temperature in the control cycle did not exceed the collapse temperature (FIG. 3) until the end of primary drying when thermocouple started losing contact with the ice and Pirani sensor reading approached the capacitance manometer reading.

To prove the concept that freeze-drying at the collapse temperature is not as dramatic as was anticipated for the amorphous materials, eight more molecules in the same formulation were freeze-dried using the same cycle as shown in FIG. 1. Exemplary data for 9 molecules (including Molecule G) are summarized in Table 1. The data in Table 1 shows that despite the stress that the molecules experienced during aggressive cycle (FIG. 1), residual moisture and glass transition temperatures were similar to the cycle that was performed below the Tg' (control cycle). Most importantly, degradation rate (shown as increase in percentage of HMW) of collapsed samples was also similar to that of the control material. No difference in reconstitution time between control and collapsed materials was observed for all 9 molecules. Therefore, freeze-drying at collapse temperature is possible, especially at high protein concentrations such as 50 mg/ml or higher, even for formulations that also contain buffers and sucrose, which normally have low glass transition temperatures.

It should be mentioned, that all materials examined in this example were amorphous, which was confirmed with the powder X-Ray Diffraction.

TABLE 1

Residual moistures, glass transition temperatures and increase in High Molecular Weight (HMW, SE-HPLC) species for 9 molecules freeze-dried using cycle in FIG. 1.

| Molecule | Initial Moisture (%) control | aggressive | Tg (° C.) control | aggressive | delta % HMW (4 wks/50° C.) control | aggressive |
|---|---|---|---|---|---|---|
| A | 0.5% | 0.5% | 86 | 85 | 0.17% | 0.16% |
| B | 0.7% | 0.7% | 87 | 86 | 0.7% | 0.7% |
| C | 0.4% | 0.7% | 85 | 85 | 0.7% | 0.7% |
| D |  |  |  |  |  | −0.3% |
| E | 0.4% | 0.2% | 91 | 95 | 1.2% | 1.2% |
|  |  |  | 64 | 59 |  |  |
| F | 0.7% | 0.5% | 84 | 86 | 0.8% | 1.2% |
| G | 0.37% | 0.36% | 89 | 88 | 0.5% | 0.5% |
| H | 0.31% | 0.33% | 94 | 73 | Above and below 3 months, 40° C. | |
|  |  |  | 48 | 45 | 0.7% | 0.7% |
| I | 0.76% | 0.18% | 86 | 80 | 0.33% | 0.59% |

Figure 4:
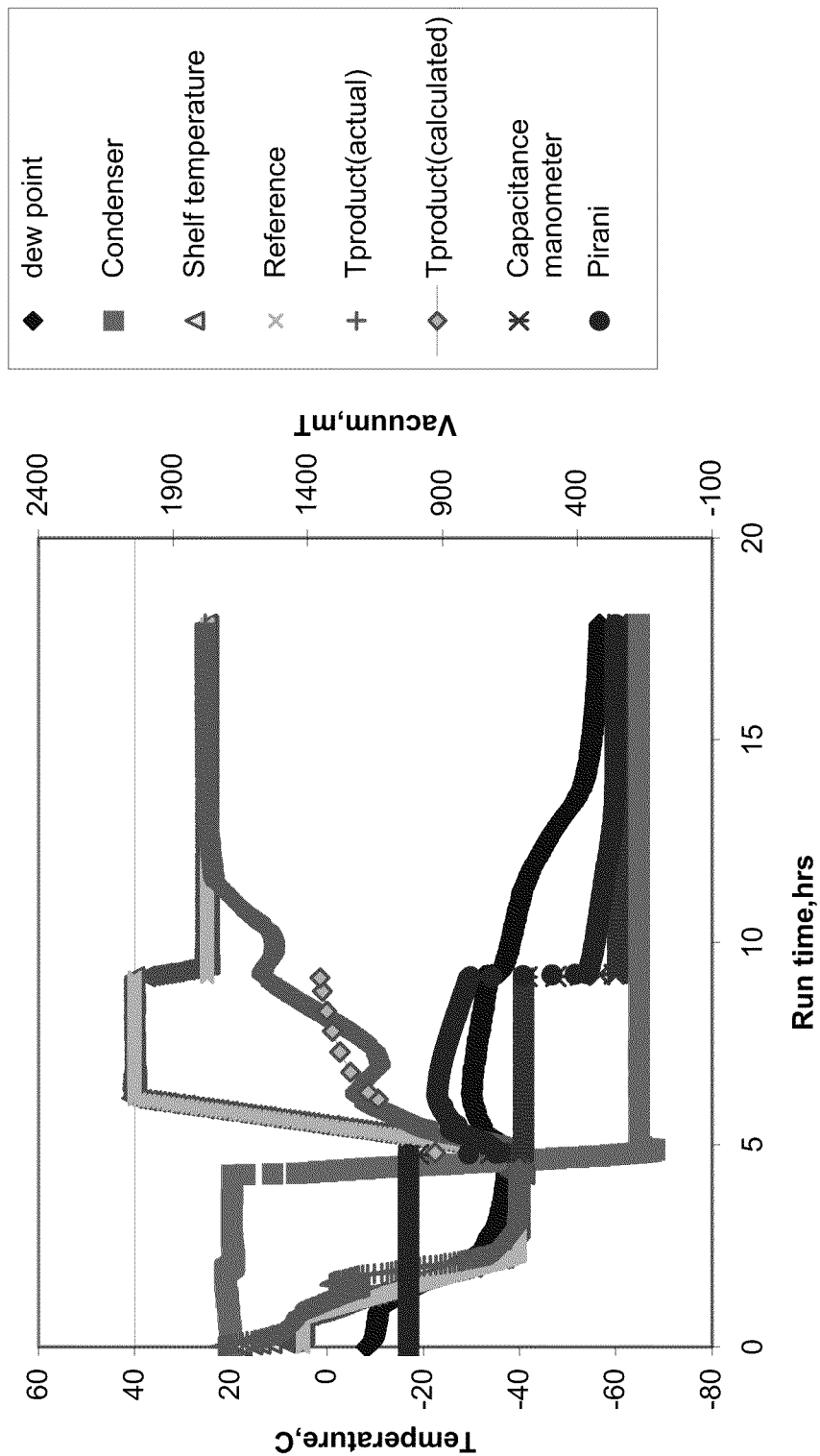
FIG. 4 illustrates an exemplary freeze-drying cycle graph of molecule G above collapse temperature but below the eutectic temperature: super aggressive cycle.
Figure 5:
FIG. 5 illustrates an exemplary cake appearance of molecule G lyophilized using super aggressive cycle from FIG. 3. Right vial represent sample from the super aggressive cycle, left vial is the sample form the control cycle.

In order to further investigate the effect of collapse on amorphous materials at high protein concentration, molecule G was lyophilized at condition where almost all primary drying was performed above the collapse temperature (referred to as super aggressive cycle) (FIG. 4). In this cycle, the product temperature was above collapse (−15° C.) but below the melting point of the ice-protein-sucrose eutectic (−3° C.). As one can see (FIG. 5), almost half of the cake was collapsed during freeze-drying. The residual moisture was 0.76%, which is 2-fold higher than the residual moisture of samples from the control cycle (FIG. 3) or even aggressive cycle (FIG. 1). Despite the visual collapse, the reconstitution time of a sample from the super aggressive cycle (FIG. 4) was similar to a sample from the control cycle (FIG. 3). Most importantly, there was no apparent increase in HMW species during storage at 4° C. and 25° C. for at least 8 months as compared to that of the samples from the control cycle (Table 2). Therefore, samples from super aggressive cycle (lyophilized well above collapse temperature) are as stable as samples from the control cycle (lyophilized below the collapse temperature). Additionally, the residual moisture of samples from the super aggressive cycle were below 1%.

TABLE 2

Comparison of the stability profile between molecule G samples lyophilized using super aggressive cycle (FIG. 4) and control cycle (FIG. 3)

| Cycle | Storage temperature, °C | High molecular weight species measured by SE-HPLC (%) | | | |
|---|---|---|---|---|---|
| | | $T_0$ | 3 months | 6 months | 8 months | 9 months |
| Control cycle (RM = 0.37 ± 0.01%) | 4 | 2.8 | 2.5 | 3.3 | — | 2.8 |
| | 25 | | 2.7 | 3.6 | — | 3.2 |
| | 40 | | 3.3 | 4.4 | — | 4.4 |
| Super aggressive cycle (RM = 0.76 ± 0.02%) | 4 | 3.2 | — | — | 2.8 | — |
| | 25 | | — | — | 2.9 | — |
| | 40 | | — | — | 4.5 | — |

Note:
Variability in HMW is due to vial-to-vial variation and variability of assay.
RM is the residual moisture of lyophilized samples.

Figure 6:
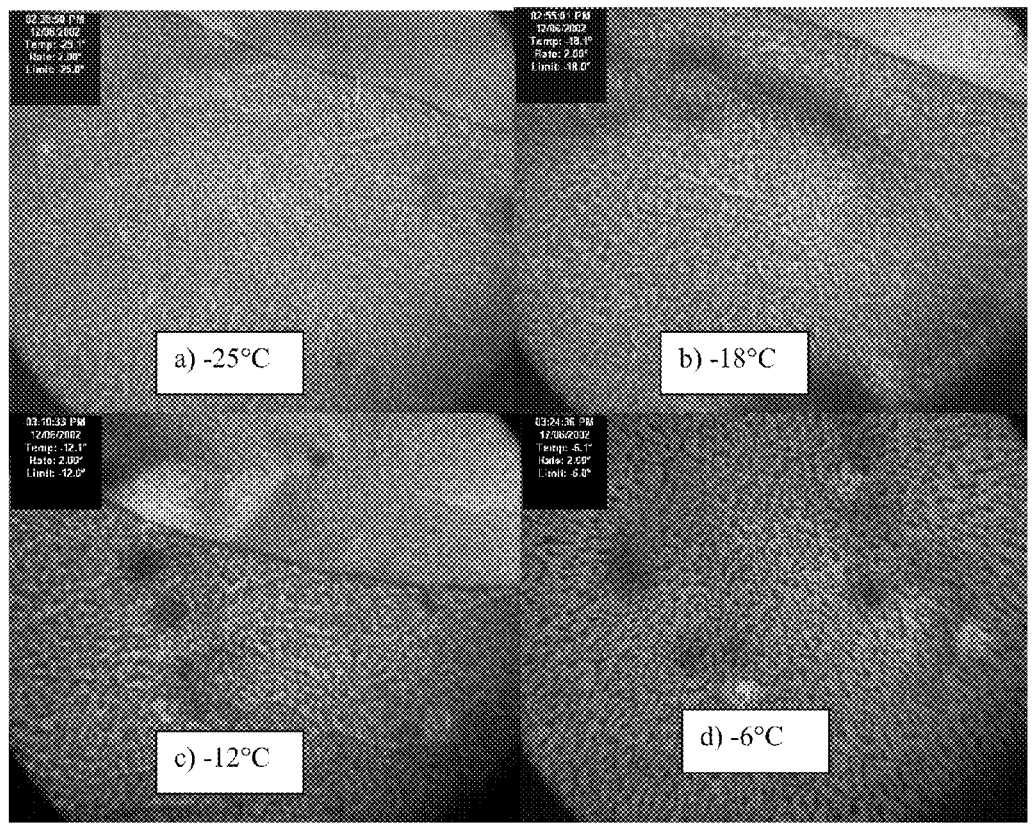
FIG. 6 illustrates exemplary freeze-drying microscopy images of 10 mg/ml protein J in TMS buffer (10 mM Tris, 4% Mannitol, 1% Sucrose).

Example 2: Freeze-Drying at or Above Collapse Temperature for Crystalline/Amorphous Materials A pharmaceutical protein J was formulated at a concentration of 10 mg/ml in a TMS buffer containing 10 mM Tris, 4% mannitol, 1% sucrose, pH 7.4 (TMS). The Tg' for this formulation was −22.6° C. Samples were lyophilized at a product temperature well below the glass transition temperature as well as well above Tg'. FIG. 6 shows exemplary images from freeze-drying microscopy of 10 mg/ml protein J in TMS lyophilized below glass transition temperature (−25° C.) and well above Tg' (i.e., −18° C., −12° C. and −6° C.).

Despite the absence of gross collapse during freeze-drying at temperatures well above the Tg', a structural change (seen as increase in pore sizes) was observed starting from −18° C. (beginning of collapse) and becoming very obvious at −6° C. Therefore, −18° C. is considered the collapse temperature for 10 mg/ml protein J in TMS.

Figure 7:
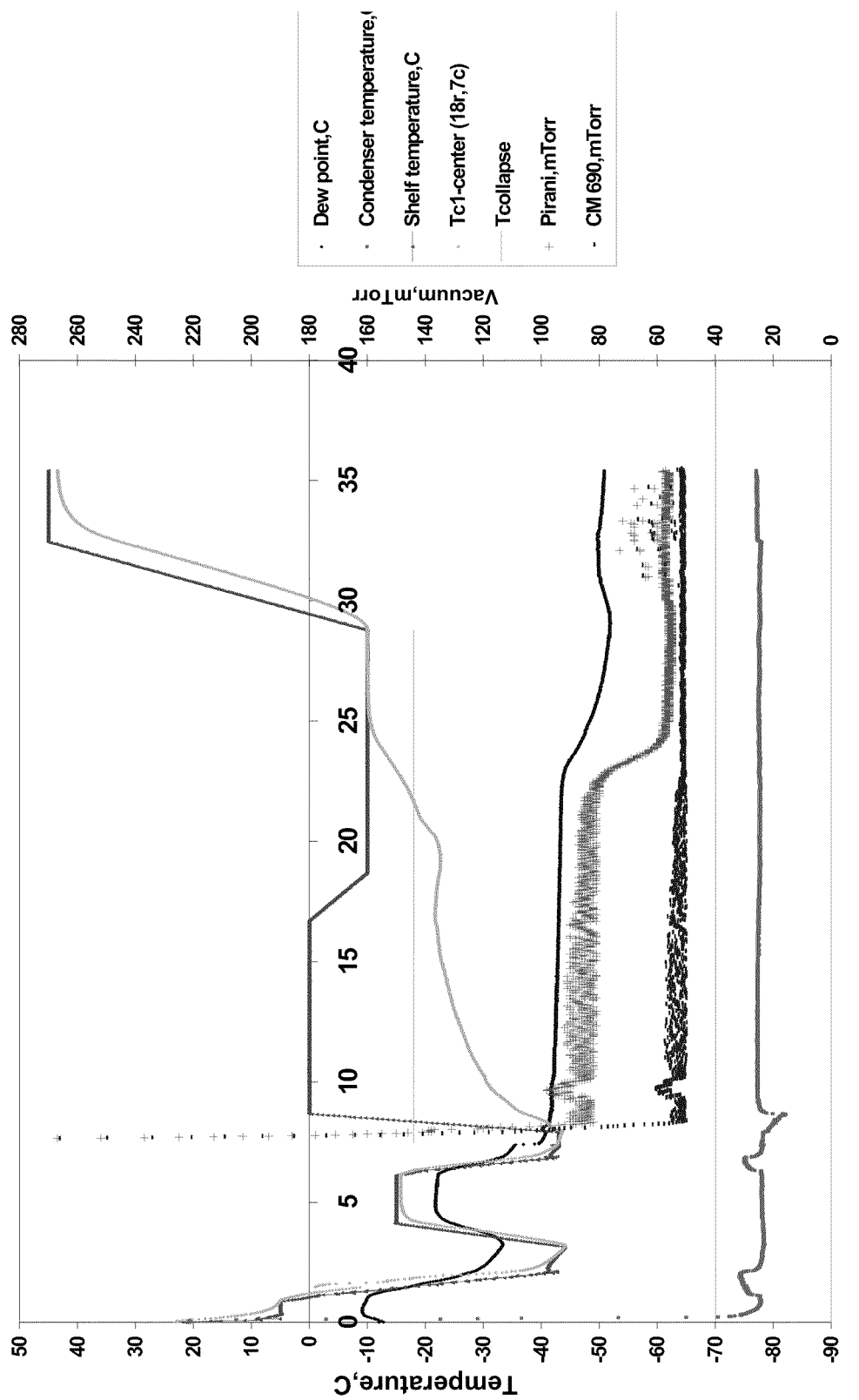
FIG. 7 illustrates an exemplary lyophilization cycle for 10 mg/ml protein J in TMS buffer performed below the onset of collapse temperature of −18° C.: working cycle 1.
Figure 8:
FIG. 8 illustrates exemplary cake appearance of 10 mg/ml protein J in TMS after working cycle 1. Residual moisture is 0.1%.
Figure 9:
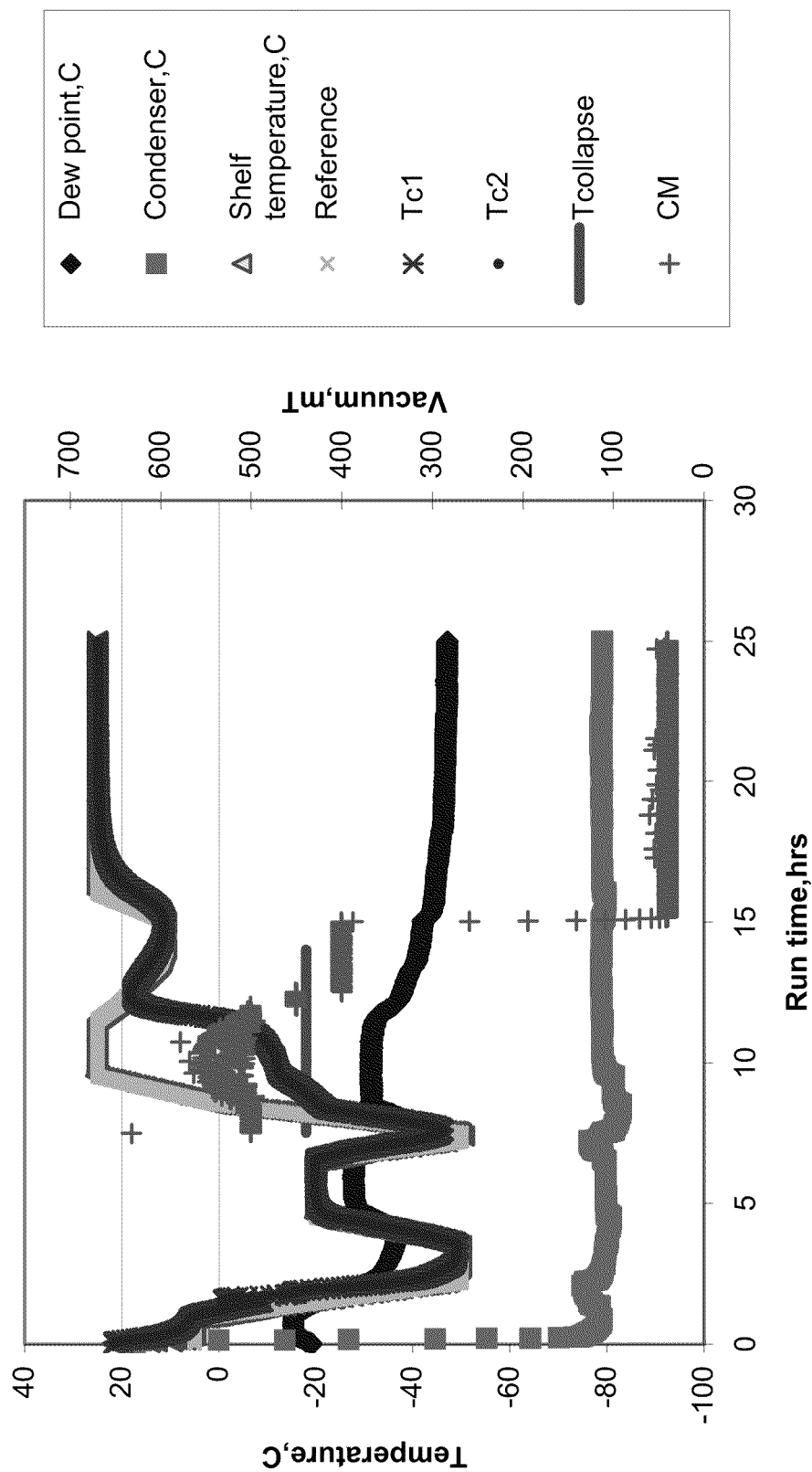
FIG. 9 illustrates protein J at 10 mg/ml in TMS: freeze-drying well above collapse temperature but below the melting point of mannitol
Figure 10:
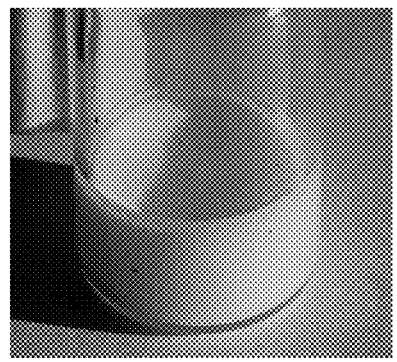
FIG. 10 illustrates exemplary cake appearance of 10 mg/ml protein J in TMS lyophilized well above the collapse temperature of amorphous phase. Residual moisture is 0.14%.

Two lyophilization cycles were performed: one cycle including a primary drying step below the collapse temperature of −18° C. (onset of collapse) and the other including a primary drying step well above collapse but below the melting point of mannitol. The first cycle (working cycle 1, FIG. 7), produces a nice cake with a small degree of shrinkage (FIG. 8). The second cycle (FIG. 9) was preformed under very aggressive conditions resulting in product temperature being above the collapse temperature of −18° C. for almost the entire primary drying step. However, the cake appearance (FIG. 10) was acceptable.

The residual moisture of the samples freeze-dried below the collapse temperature is comparable to that of the samples freeze-dried above the collapse. For example, the residual moisture of the samples freeze-dried below the collapse temperature was about 0.1% and the residual moisture of the samples freeze-dried above the collapse temperature was about 0.14%. In addition, the reconstitution time and even cake appearance of the samples freeze-dried above the collapse temperature were similar to those of the samples freeze-dried below the collapse temperature.

Importantly, the stability of materials lyophilized well above the collapse temperature was notably better compared to that of the control material (freeze-dried below the collapse temperature). For example, Table 3 shows that, when stored at 40° C., the collapsed material was much more stable compared to the control material (lyophilized below the collapse). Without wishing to be bound by any theories, one hypothesis is that protein undergoes refolding or "annealing" when freeze-dried above the collapse temperature, resulting in improved stability.

TABLE 3

Stability of pharmaceutical protein drug J lyophilized at 10 mg/ml in TMS during storage at elevated temperatures.

| | Storage temperature, °C | % HMW at $T_0$ | % HMW at 6 months | % HMW at 12 months |
|---|---|---|---|---|
| Working cycle 1 (below collapse) | 4 | 1.7 | 1.8 | 2.2 |
| | 25 | | 2.1 | 2.7 |
| | 40 | | 3.0 | 4.3 |
| Robustness cycle (above collapse) | 4 | 0.9 | 0.9 | 0.7 |
| | 25 | | 1.1 | 0.9 |
| | 40 | | 2.0 | 2.4 |

To summarize the data above, it is contemplated that, for highly concentrated proteins, freeze-drying above the collapse temperature of amorphous phase (producing micro-collapse, but no gross visually detected cake collapse) can lead to improved product stability, in particular, if the residual moisture is within specification.

Example 3: Freeze Drying Multi-Valent Vaccine Polysaccharide at or Above the Collapse Temperature In this example, an unconjugated polysaccharide of one of the serotypes of Pneumococcal 13-Valent vaccine (Serotype X) was freeze-dried at three different temperatures during primary drying. The first temperature was below the collapse temperature, the second was slightly above the collapse temperature and the third was approximately 10° C. above the collapse temperature. The lyophilization formulation contained the polysaccharide, sucrose and Diphtheria CRM 197 protein, with a total dry solids content of 6.5%. Freeze-drying was performed in 50-ml Schott tubing vials filled with 5 ml of solution. Residual moisture, glass transition temperature, reconstitution time, and conjugation efficiency of reconstituted material were the quality attributes used to evaluate lyophilized product freeze-dried under conditions shown below. The target values for these attributes are: a residual moisture of ≤5%, a glass transition temperature of ≥20° C., and a reconstitution time of ≤1 minute.

Figure 11:
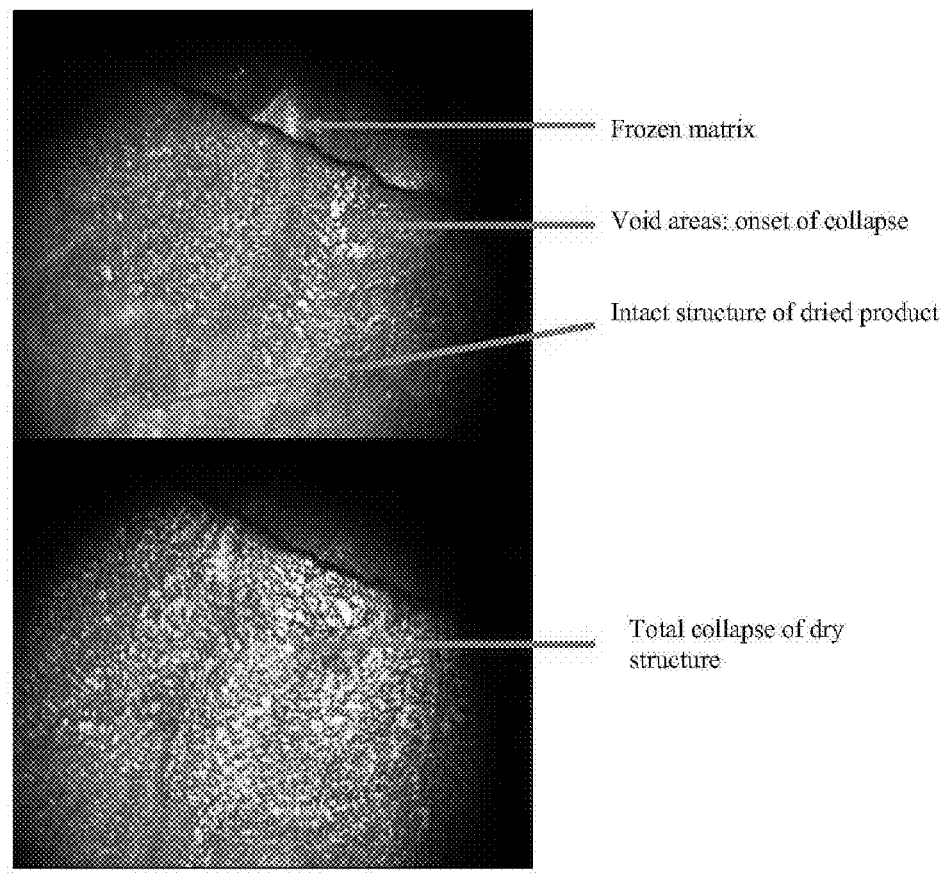
FIG. 11 illustrates exemplary formation of the void areas during the isothermal hold at −34° C. (Top picture) indicating the beginning of collapse at the sublimation front. Total collapse of structure upon lyophilization happened during the isothermal hold at −33° for 30 min (bottom picture).

Prior to freeze-drying, thermal analysis was performed to measure the glass transition and the collapse temperatures of the Serotype X solution. The glass transition temperature, measured as a middle point of the transition by modulated Differential Scanning Calorimetry ("DSC") (Q1000, TA Instruments, New Castle, Del.), was −34.7° C. Freeze-drying microscopy ("FDM"), performed with Linkam FDCS-196 (Surrey, UK) stage attached to the Nikon Eclipse E600 (Melville, N.Y.) microscope, showed that small void areas in a structure of freeze-dried matrix began forming when the temperature was raised to −34° C. (Top picture, FIG. 11). When the product temperature was increased to −33° C., the structure of dry product at sublimation surface began collapsing. Therefore, the microscopic collapse temperature for this particular formulation was −33° C., less than 2° C. above the glass transition temperature. Both DSC and FDM showed that the onset of melting endotherm was approximately −2.7° C.

Baseline Freeze-Drying Cycle—Below Collapse Temperature

Figure 12:
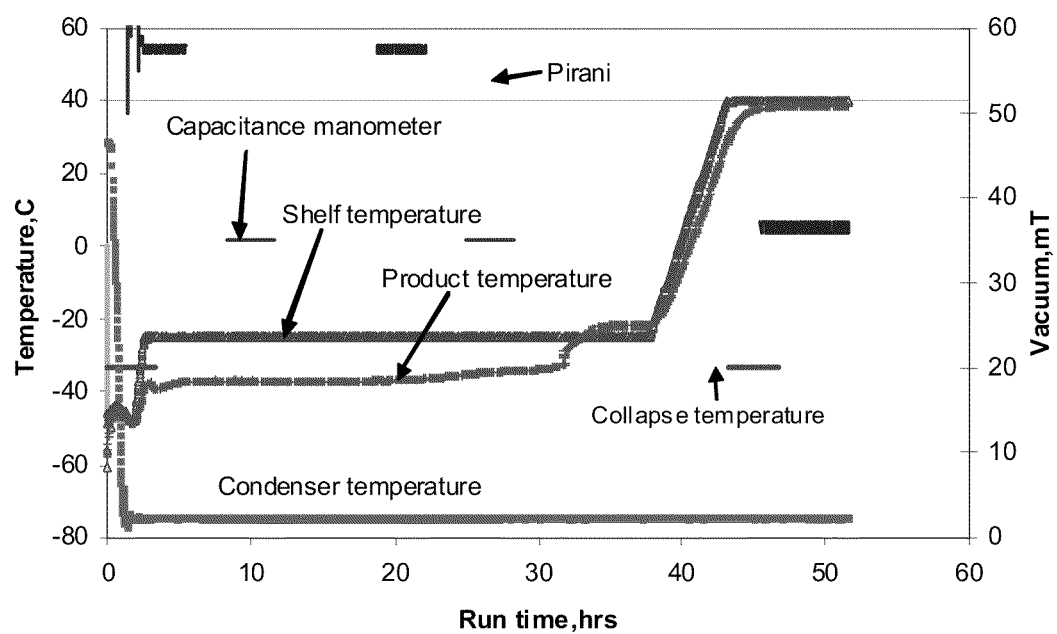
FIG. 12 illustrates exemplary freeze-drying of Serotype X formulation in 50-ml Schott tubing vials. The cake height was approximately 0.5 cm. The lyophilization cycle was performed on Benchmark 1000 lyophilizer (SP Industries).
Figure 13:
FIG. 13 illustrates exemplary cake appearance of Serotype X lyophilized below the collapse temperature.

The baseline freeze-drying cycle was performed at a product temperature close to −37° C. (FIG. 12), well below the collapse temperature. Freezing was performed in ethanol-dry ice bath; vials with frozen material were loaded on pre-chilled (−50° C.) shelves of Benchmark 1000 lyophilizer (SP Industries, Gardiner, N.Y.). Primary drying was completed prior to the secondary drying ramp. The residual moisture of lyophilized material was low, 0.08±0.01%. Two glass transition temperatures were detected: a smaller one at 63° C. and a larger one at 84° C. Despite shrinkage, cake appearance was acceptable (FIG. 13). Reconstitution of lyophilized material was rapid (less than 1 minute, including time for the solution to clear after reconstitution). Conjugation efficiency of lyophilized material was within acceptable range (Table 4). However, the lyophilization cycle was very long (approximately 52 hours) considering the cake height was only 0.5 cm.

Freeze-Drying Slightly Above Collapse Temperature (Collapse Study 1)

Figure 14:
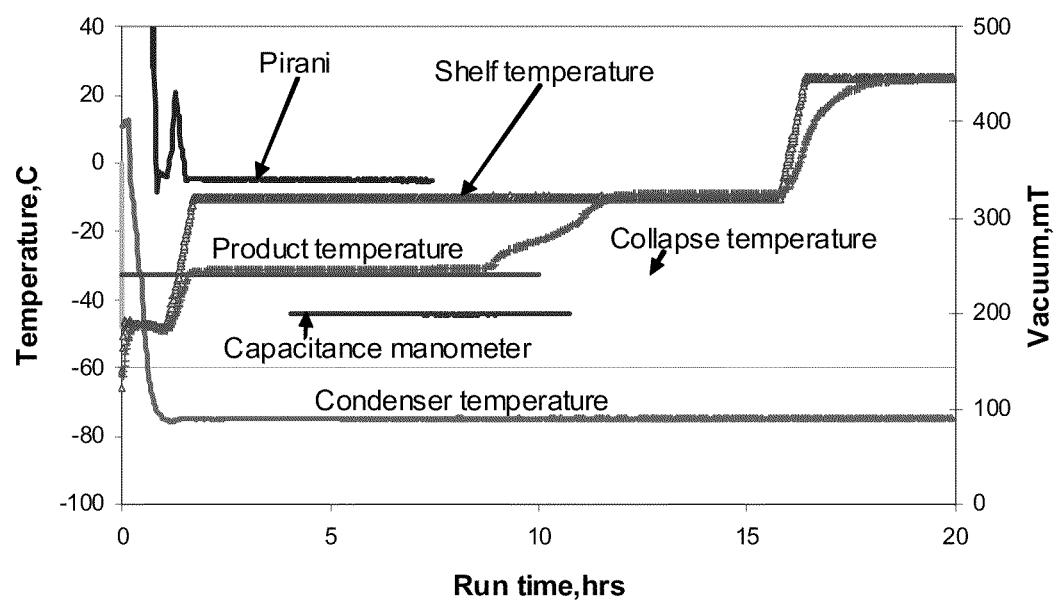
FIG. 14 illustrates an exemplary freeze-drying cycle used to lyophilize Serotype X polysaccharides which maintained product temperature slightly above the collapse temperature (collapse study 1).

When the same material was freeze-dried slightly above the collapse temperature (maintaining the product temperature during primary drying at approximately −31° C.), cycle time was decreased to 20 hours (FIG. 14). The residual moisture of the lyophilized material was 3.69±0.13%, and had a low glass transition temperature of 44° C. The combination of collapse phenomenon and decreased secondary drying temperature, from 40° C. (See FIG. 12) to 25° C. (See FIG. 14) contributed to the higher residual moisture, as compared to the baseline cycle. In further comparison to the baseline freeze-drying cycle (see the Collapse study 1 above), the cake appearance was only slightly altered by the collapse phenomenon (FIG. 15, left vial) while reconstitution time was not affected. Biochemical characteristics with respect to conjugation efficiency of material manufactured slightly above collapse temperature were within specification (Table 4).

Freeze-Drying about 10° C. Above Collapse Temperature (Collapse Study 2)

Figure 15:
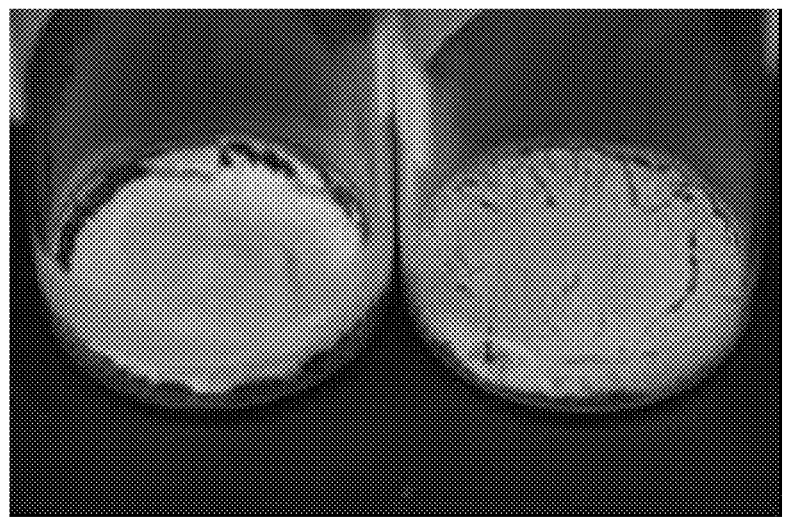
FIG. 15 illustrates exemplary cake appearance of Serotype X polysaccharides freeze-dried slightly above collapse temperature (collapse study 1, left vial) and well above the collapse temperature (collapse study 2, right vial).
Figure 16:
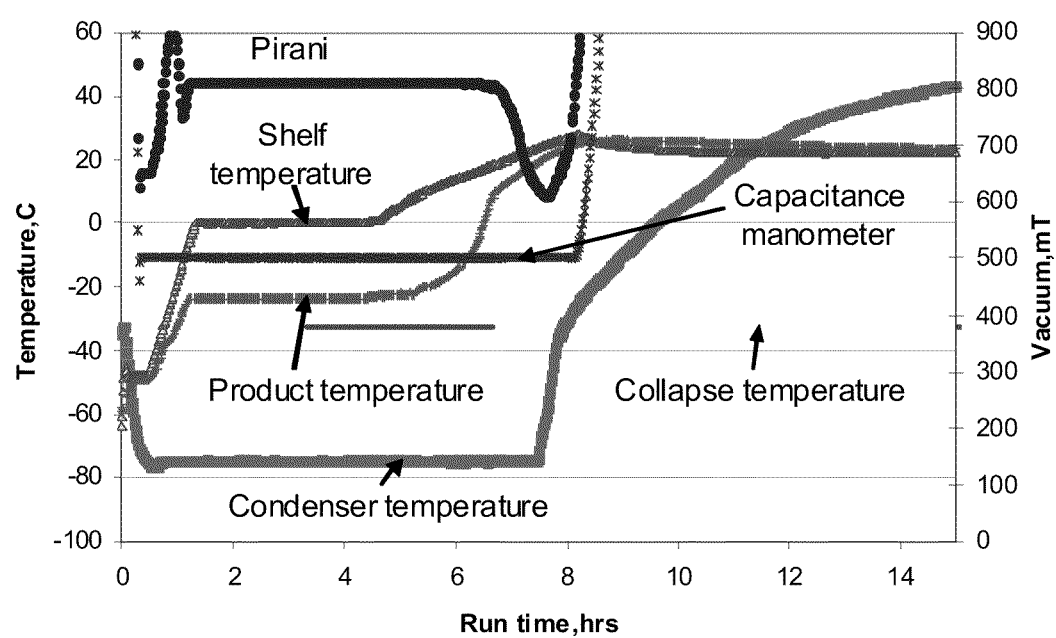
FIG. 16 illustrates an exemplary freeze-drying cycle used to lyophilize Serotype X polysaccharides above the collapse temperature (collapse study 2).

To assess the effect of gross collapse on the quality of lyophilized material, Serotype X solution was freeze-dried in the same freeze-dryer in the same container (with the same fill volume), but at a product temperature almost 10° C. higher than the collapse temperature (cycle example is shown in FIG. 16). Primary drying was completed in 8 hours, much less time when compared to 35 hours for the baseline cycle (FIG. 12) and still less than the 10 hours for collapse study 1 (FIG. 14). To impart more stress on the product, the refrigeration system was shut down at the end of primary drying while leaving the vacuum pump on (FIG. 16). This combination of stresses resulted in a very high residual moisture of 6.12±0.15% and poor cake appearance as compared to the other lyophilized materials disclosed herein (FIG. 15, right vial). Glass transition temperature of lyophilized material after collapse study 2 (FIG. 16) was 20° C., low in comparison to the other lyophilization cycles. Despite the elevated moisture and poor cake appearance, reconstitution was still less than 1 minute. Most importantly, biochemical characteristics of the reconstituted material manufactured well above collapse temperature met almost all acceptance criteria with respect to conjugation efficiency (Table 4). Without wishing to be bound by any theories, it is contemplated that some lyophilized biological materials can be easily reconstituted even after freeze-drying at extreme conditions (e.g., approximately 110° C. above the collapse temperature) while maintaining their important properties. The product temperature during this treatment remained below the melting point of ice-freeze-concentrate eutectic. Thus, freeze-drying above collapse temperature but below the melting point can be very beneficial from an economical perspective, because of the significant reduction in process time, if the quality of lyophilized material remains acceptable.

Evaluation of Conjugation Efficiency

The quality of the lyophilized polysaccharides was assessed by the ability of the polysaccharides to conjugate with a carrier protein (e.g., conjugation efficiency) using standard methods known in the art. In this example, lyophilized polysaccharides are reconstituted and conjugated to a carrier protein $CRM_{197}$. Conjugation efficiency was determined using the following criteria:

(1) Saccharide-to-Protein Ratio ("SPR"): an indicator of the reproducibility and efficiency of the conjugation reaction, and is obtained by dividing the saccharide content by the protein content;

(2) percent (%) saccharide≤0.3 Kd ("0.3 Kd"): molecular size distribution established by size exclusion chromatography as determined by polysaccharide content;

(3) percent free saccharide ("% FS"): the portion of total saccharide that is non-covalently bound to the carrier protein;

(4) percent free protein—Capillary Electrophoresis ("% FP-CE"): the portion of carrier protein ($CRM_{197}$) that is not conjugated to a saccharide, tested via Capillary Electrophoresis.

(5) Adjustable yield: Adjusted yield based upon estimated % FS.

Exemplary properties of lyophilized and reconstituted polysaccharides are shown in Table 4.

TABLE 4

Properties of lyophilized and reconstituted polysaccharide X

| | | Material freeze-dried | | |
|---|---|---|---|---|
| Parameter | Acceptable range | Below collapse temperature (FIG. 12) | 2° C. above collapse temperature (FIG. 14) | 10° C. above collapse temperature (FIG. 16) |
| Properties of lyophilized powder | | | | |
| Residual moisture, % | <5% | 0.08% | 3.69% | 6.12% |
| Glass transition temperature, ° C. | ≥20° C. | 63/84° C. | 44° C. | 20° C. |
| Reconstitution time | <1 minute | <1 minute | <1 minute | <1 minute |
| Properties of reconstituted material | | | | |
| SPR | 1.2-2.0 | 1.5 | 1.5 | 1.4 |
| 0.3 Kd | 45-70% | 56% | 58% | 40%* |
| % FS | 13-28% | 21% | 22% | 22% |
| % FP-CE | <6.6% | 1.7% | 1.6% | 1.7% |
| Adj. Yield | 32-54% | 43% | 40% | 35% |

*low Kd value was likely due to insufficient recovery during reconstitution but not due to the quality of material itself (confirmed by 4 different methods).

In summary, this example has established that multivalent vaccine components (e.g., polysaccharides) can be lyophilized with a product temperature at or above the collapse temperature. Lyophilized productions from this process have comparable quality when compared to material lyophilized with product temperature below the collapse temperature. Further, the overall lyophilization process takes less time when the product temperature during primary drying is at or above the collapse temperature.

Example 4: Freeze Drying Live Virus Vaccine Above Collapse Temperature

Figure 17:
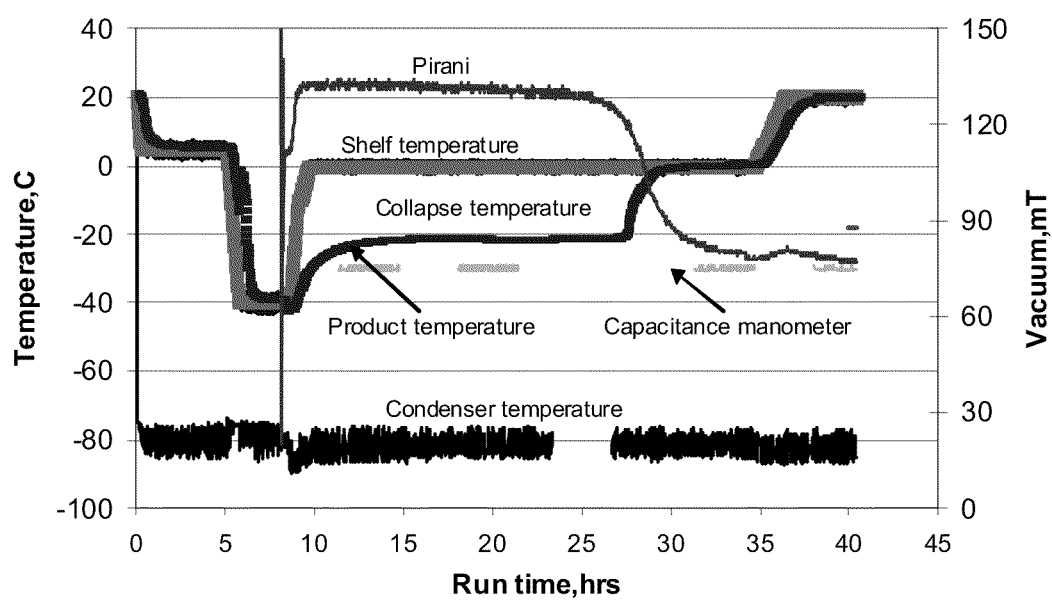
FIG. 17 illustrates an exemplary freeze-drying cycle used to lyophilize chicken vaccine below the collapse temperature.
Figure 18:
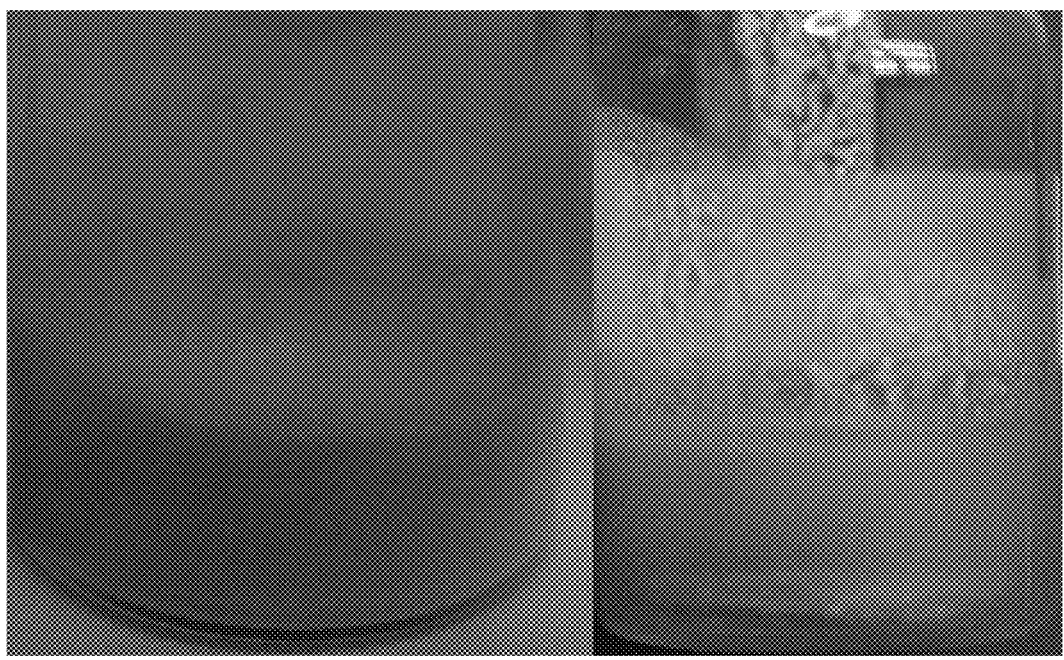
FIG. 18 illustrates exemplary cake appearance of lyophilized chicken vaccine. Left vial contains a cake freeze-dried below the collapse temperature. Right vial contains a cake freeze-dried above the collapse temperature (the loss of structure could be seen on the bottom of the cake).
Figure 19:
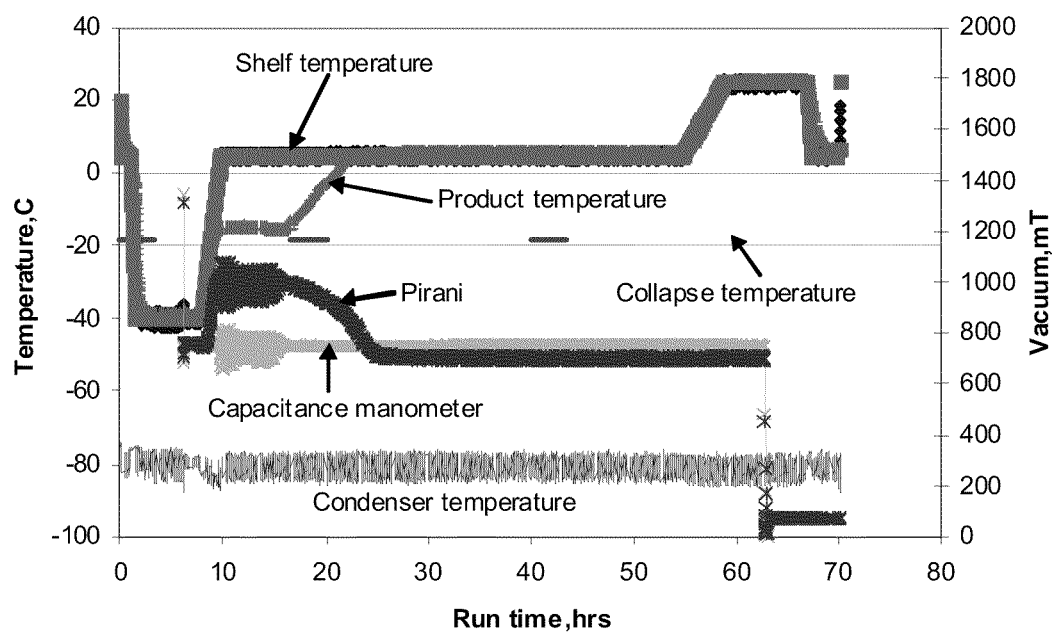
FIG. 19 illustrates an exemplary freeze-drying cycle used to lyophilize chicken vaccine above the collapse temperature.
Figure 20:
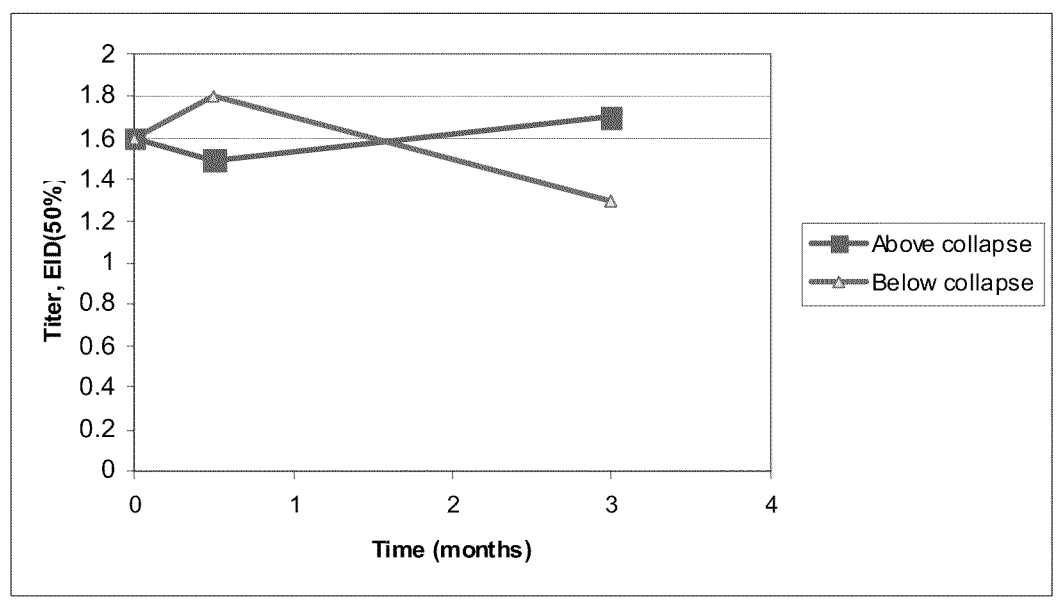
FIG. 20 illustrates exemplary stability analysis results of chicken vaccine during storage at 37° C. Filled squares represent materials freeze-dried above the collapse temperature, open triangles represent materials freeze-dried below the collapse temperature.

In this example, a live-virus young chicken vaccine was lyophilized both above and below the collapse temperature, and the results compared. The quality of vaccine was assessed by cake appearance, residual moisture and titer stability after storage at 37° C. for 3 months. The glass transition temperature was −26.8° C. measured by modulated DSC. The collapse temperature of −18° C. was measured by freeze-drying microscope (Linkam stage). An exemplary lyophilization cycle performed below the collapse temperature is shown in FIG. 17. The cake appearance of lyophilized material was acceptable (FIG. 18, left vial). The residual moisture was 0.5±0.05%. When the product was freeze-dried above the collapse temperature (FIG. 19), some visible collapse of lyophilized cake was observed. The loss of structure was visible at the bottom of the cake (FIG. 18, right vial). Because the cycle was long, the residual moisture of collapsed material was low, 0.24%. The reconstitution time for both materials was comparable. Moreover, the stability of material lyophilized above the collapse temperature was better than stability of material produced below the collapse temperature. For examples, titer data shown in FIG. 20 after 3 months of storage shows improved stability for the material lyophilized at a product temperature during primary drying above the collapse temperature. Furthermore, the primary drying time in the cycle performed above the collapse temperature was shorter compared to the cycle below collapse temperature. Thus, the experiments in this example have once again established that collapse during freeze-drying appears to have minimal effect on important quality attributes of biological materials. In some instances, lyophilization above collapse may improve certain properties of lyophilized products.

EQUIVALENTS

The foregoing has been a description of certain non-limiting embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

INCORPORATION BY REFERENCE

All publications and patent documents cited in this application are incorporated by reference in their entirety for all purposes to the same extent as if the contents of each individual publication or patent document were incorporated herein.

What is claimed is:

1. A method of lyophilizing a pharmaceutical substance in an aqueous liquid formulation, comprising:
   (a) a freezing step, wherein water in the liquid formulation is converted to ice,
   (b) followed by a primary drying step conducted in a lyophilizer, characterized in that the primary drying step consists of removing water in the pharmaceutical substance by direct sublimation, and is executed at a product temperature at or above the macro-collapse temperature without avoiding cake macro-collapse, and at a pressure below about 500 mTorr,
wherein macro-collapse temperature is the temperature at which the lyophilized cake has visually detectable collapse, and is at least 5° C. above the mid-point of glass transition temperature (Tg');

wherein the lyophilized pharmaceutical substance is suitable for later reconstitution to a biologically or pharmaceutically active substance; and wherein said pharmaceutical substance is at a concentration of at least 10 mg/ml in said aqueous liquid formulation.

2. The method of claim 1, wherein the pharmaceutical substance is selected from the group consisting of a protein, a peptide, a polysaccharide, a small molecule, a natural product, a nucleic acid, an immunogen, a vaccine, a polymer, a chemical compound, and a combination thereof.

3. The method of claim 1, wherein the primary drying step is performed at a product temperature that is below the onset temperature of the melting endotherm of the frozen formulation of step (a).

4. The method of claim 3, further comprising determining the onset temperature of the melting endotherm of the frozen formulation by Differential Scanning calorimetry (DSC).

5. The method of claim 1, wherein the pharmaceutical substance is at a concentration of at least 50 mg/ml in the liquid formulation.

6. The method of claim 1, wherein the pharmaceutical substance is at a concentration of at least 100 mg/ml in the liquid formulation.

7. The method of claim 1, wherein the lyophilized product comprises amorphous materials.

8. The method of claim 1, wherein the lyophilized product comprises partly crystalline/partly amorphous materials.

9. The method of claim 1, wherein the liquid formulation is a sucrose-based formulation.

10. The method of claim 1, wherein the freezing step produces a solid product with a product temperature of about −20° C. to about −70° C.

11. The method of claim 1, wherein the freezing step produces a solid product with a product temperature of about −40° C. to about −70° C.

12. The method of claim 1, wherein the primary drying step is performed at a pressure below about 200 mTorr.

13. The method of claim 1, wherein said liquid formulation comprises histidine, sucrose, and mannitol.

14. The method of claim 1, wherein the pharmaceutical substance is at a concentration of at least 20 mg/ml in the liquid formulation.

15. The method of claim 1, wherein said lyophilizer is a commercial-scale lyophilizer.

16. A method of lyophilizing a pharmaceutical substance in an aqueous liquid formulation, comprising:
   (a) a freezing step, wherein water in the liquid formulation is converted to ice,
   (b) followed by a primary drying step conducted in a lyophilizer, characterized in that the primary drying step consisting of removing water in the pharmaceutical substance by direct sublimation, and is executed at a product temperature at or above the macro-collapse temperature without avoiding cake macro-collapse, and at a pressure below about 500 mTorr,
wherein macro-collapse temperature is the temperature at which the lyophilized cake has visually detectable collapse, and is at least 3° C. above the mid-point of glass transition temperature (Tg');

wherein the lyophilized pharmaceutical substance is suitable for later reconstitution to a biologically or pharmaceutically active substance, wherein the liquid formulation comprises a stabilizing agent, wherein said pharmaceutical substance is at a concentration of at least 10 mg/ml in said aqueous liquid formulation, and wherein the ratio of the mass amount of the stabilizing agent and said pharmaceutical substance is no greater than 1000.

17. The method of claim 16, wherein the pharmaceutical substance is at a concentration of at least about 20 mg/ml in the liquid formulation.

18. The method of claim 16, wherein the pharmaceutical substance is at a concentration of at least 50 mg/ml in the liquid formulation.

19. The method of claim 16, wherein the stabilizing agent is selected from the group consisting of sucrose, mannose, sorbitol, raffinose, trehalose, mannitol, sodium chloride, arginine, lactose, hydroxyethyl starch, dextran, polyvinylpyrolidone, glycine, and a combination thereof.

20. The method of claim 16, wherein the lyophilized product comprises amorphous materials.

21. The method of claim 16, wherein the lyophilized product comprises partly crystalline/partly amorphous materials.

22. The method of claim 16, wherein the pharmaceutical substance is selected from the group consisting of a protein, a peptide, a polysaccharide, a small molecule, a natural product, a nucleic acid, an immunogen, a vaccine, a polymer, a chemical compound, and a combination thereof.

23. The method of claim 22, wherein the pharmaceutical substance is a protein.

24. The method of claim 23, wherein the protein is selected from the group consisting of an antibody or a fragment thereof, a growth factor, a clotting factor, a cytokine, a fusion protein, an enzyme, a carrier protein, a polysaccharide-containing antigen, a Small Modular ImmunoPharmaceutical, and a combination thereof.

25. The method of claim 24, wherein the antibody is a monoclonal antibody or a single-domain antibody.

26. The method of claim 16, wherein the liquid formulation is formulated such that the macro-collapse temperature is at least 5° C. higher than the middle point of glass transition temperature (Tg').

27. The method of claim 16, wherein the pharmaceutical substance is at a concentration of at least 100 mg/ml in the liquid formulation.

28. The method of claim 16, wherein said lyophilizer is a commercial-scale lyophilizer.

29. A method of lyophilizing a pharmaceutical substance in an aqueous liquid formulation, wherein said pharmaceutical substance is a protein, comprising:
(a) a freezing step, wherein water in the liquid formulation is converted to ice,
(b) followed by a primary drying step conducted in a lyophilizer, characterized in that the primary drying step consists of removing water in the pharmaceutical substance by direct sublimation, and is executed at a product temperature at or above the macro-collapse temperature without avoiding cake macro-collapse, and at a pressure below about 500 mTorr,
wherein macro-collapse temperature is the temperature at which the lyophilized cake has visually detectable collapse, and is at least 3° C. above the mid-point of glass transition temperature (Tg');
wherein the lyophilized pharmaceutical substance is suitable for later reconstitution to a biologically or pharmaceutically active substance; and
wherein said pharmaceutical substance is at a concentration of at least 10 mg/ml in said aqueous liquid formulation.

30. The method of claim 29, wherein the protein is selected from the group consisting of an antibody or a fragment thereof, a growth factor, a clotting factor, a cytokine, a fusion protein, an enzyme, a carrier protein, a Small Modular ImmunoPharmaceutical, and a combination thereof.

31. A method of storing a pharmaceutical substance comprising:
(a) lyophilizing the pharmaceutical substance in an aqueous liquid formulation, comprising:
(i) a freezing step, wherein water in the pharmaceutical substance is converted to ice,
(ii) followed by a primary drying step conducted in a lyophilizer, characterized in that the primary drying step consists of removing water in the pharmaceutical substance by direct sublimation, and is executed at a product temperature at or above the macro-collapse temperature without avoiding cake macro-collapse, and at a pressure below about 500 mTorr,
wherein macro-collapse temperature is the temperature at which the lyophilized cake has visually detectable collapse, and is at least 3° C. above the mid-point of glass transition temperature (Tg');
wherein said pharmaceutical substance is at a concentration of at least 10 mg/ml in said aqueous liquid formulation, and
wherein the lyophilized pharmaceutical substance is suitable for later reconstitution to a biologically or pharmaceutically active substance;
(b) storing the lyophilized pharmaceutical substance for a period longer than 3 months.

32. The method of claim 31, wherein the liquid formulation is formulated such that the macro-collapse temperature is at least 5° C. higher than the middle point of glass transition temperature (Tg').

33. The method of claim 31, wherein the pharmaceutical substance is at a concentration of at least 20 mg/ml in the liquid formulation.

34. The method of claim 31, wherein the pharmaceutical substance is at a concentration of at least 50 mg/ml in the liquid formulation.

35. The method of claim 31, wherein the pharmaceutical substance is at a concentration of at least 100 mg/ml in the liquid formulation.

36. The method of claim 31, wherein said lyophilizer is a commercial-scale lyophilizer.

37. A method of lyophilizing a pharmaceutical substance in an aqueous liquid formulation, comprising:
(a) a freezing step, wherein water in the liquid formulation is converted to ice and produces a solid product with a product temperature of about −40° C. to about −70° C.,
(b) followed by a primary drying step conducted in a lyophilizer, characterized in that the primary drying step removes water in the pharmaceutical substance by direct sublimation, and is executed at a product temperature at or above the macro-collapse temperature without avoiding cake macro-collapse, and at a pressure at or below about 200 mTorr,
wherein macro-collapse temperature is the temperature at which the lyophilized cake has visually detectable collapse, and is at least 3° C. above the mid-point of glass transition temperature (Tg');
wherein the lyophilized pharmaceutical substance is suitable for later reconstitution to a biologically or pharmaceutically active substance;
wherein the pharmaceutical substance comprises a protein, a peptide, a polysaccharide, a small molecule, a natural product, a nucleic acid, an immunogen, a vaccine, a polymer, a chemical compound, or a combination thereof; and
wherein the pharmaceutical substance is contained in the liquid formulation at a concentration of 50 mg/ml, the liquid formulation further comprising 5% (or 50 mg/ml) sucrose, 10 mM histidine, 10 mM methionine, and 0.01% (or 0.1 mg/ml) polysorbate 80.

38. A method of lyophilizing a pharmaceutical substance in an aqueous liquid formulation, comprising:
   (a) a freezing step, wherein water in the liquid formulation is converted to ice and produces a solid product with a product temperature of about −40° C. to about −70° C.,
   (b) followed by a primary drying step conducted in a lyophilizer, characterized in that the primary drying step removes water in the pharmaceutical substance by direct sublimation, and is executed at a product temperature at or above the macro-collapse temperature without avoiding cake macro-collapse, and at a pressure at or below about 200 mTorr, wherein macro-collapse temperature is the temperature at which the lyophilized cake has visually detectable collapse, and is at least 3° C. above the mid-point of glass transition temperature (Tg');

wherein the lyophilized pharmaceutical substance is suitable for later reconstitution to a biologically or pharmaceutically active substance;

wherein the pharmaceutical substance comprises a protein selected from the group consisting of:

an antibody or a fragment thereof, a growth factor, a clotting factor, a cytokine, a fusion protein, an enzyme, a carrier protein, a Small Modular ImmunoPharmaceutical, and a combination thereof; and wherein the pharmaceutical substance is contained in the liquid formulation at a concentration of 10 mg/ml, the liquid formulation further comprising 10 mM Tris, 4% (or 40 mg/ml) mannitol, and 1% (or 10 mg/ml) sucrose, at pH 7.4.

* * * * *